United States Patent
Dunn

(10) Patent No.: US 10,814,049 B2
(45) Date of Patent: Oct. 27, 2020

(54) NEGATIVE PRESSURE WOUND CLOSURE DEVICES AND METHODS

(71) Applicant: University of Massachusetts, Boston, MA (US)

(72) Inventor: Raymond Dunn, Shrewsbury, MA (US)

(73) Assignee: University of Massachusetts, Boston, MA (US)

(*) Notice: Subject to any disclaimer, the term of this patent is extended or adjusted under 35 U.S.C. 154(b) by 449 days.

(21) Appl. No.: 15/629,596

(22) Filed: Jun. 21, 2017

(65) Prior Publication Data
US 2017/0281838 A1     Oct. 5, 2017

Related U.S. Application Data

(63) Continuation-in-part of application No. PCT/US2016/067051, filed on Dec. 15, 2016, which
(Continued)

(51) Int. Cl.
*A61M 1/00*     (2006.01)
*A61F 13/02*     (2006.01)
*A61F 13/00*     (2006.01)

(52) U.S. Cl.
CPC ..... *A61M 1/0072* (2014.02); *A61F 13/00068* (2013.01); *A61F 13/0216* (2013.01);
(Continued)

(58) Field of Classification Search
CPC .......... A61F 13/00068; A61F 13/0216; A61M 1/0072; A61M 1/0088; A61M 2205/0216;
(Continued)

(56) References Cited

U.S. PATENT DOCUMENTS 3,194,239 A    7/1965   Sullivan
4,771,482 A *   9/1988   Shlenker ................ A61B 42/10
                                             2/161.7
(Continued)

FOREIGN PATENT DOCUMENTS

AU     2012261793 A1    1/2013
CN     101112326 A      1/2008
(Continued)

OTHER PUBLICATIONS

U.S. Appl. No. 15/066,527, filed Mar. 10, 2016, 2017-0165116, Published.
(Continued)

*Primary Examiner* — Adam Marcetich
(74) *Attorney, Agent, or Firm* — McCarter & English, LLP

(57) ABSTRACT

Systems, devices, and methods of the present application can accelerate and reduce medical complications associated with healing of non-planar wounds such as amputation wounds. The devices and methods utilize a collapsing structure and negative pressure to cause the shaped wound to preferentially close. The structure can accommodate movement over curved tissue surfaces, which can utilize scales or interleaved elements to provide efficient wound closure along arcuate paths. This structure can enable gradual closure from the deepest portion of the wound to the shallowest portion.

28 Claims, 28 Drawing Sheets

Related U.S. Application Data is a continuation-in-part of application No. 15/066,527, filed on Mar. 10, 2016, now Pat. No. 10,575,991.

(60) Provisional application No. 62/267,728, filed on Dec. 15, 2015.

(52) U.S. Cl.
CPC ... *A61M 1/0088* (2013.01); *A61M 2205/0216* (2013.01); *A61M 2205/3344* (2013.01); *A61M 2205/3379* (2013.01)

(58) Field of Classification Search
CPC .. A61M 2205/3344; A61M 2205/3379; A41D 31/245; A41D 31/24; A41D 19/0096; Y10S 428/911; F41H 5/0492
See application file for complete search history.

(56) References Cited

U.S. PATENT DOCUMENTS

| | | | |
|---|---|---|---|
| 5,368,930 A * | 11/1994 | Samples | B29C 41/14 428/323 |
| 5,415,715 A | 5/1995 | Delage et al. | |
| 5,636,643 A | 6/1997 | Argenta et al. | |
| 5,853,863 A * | 12/1998 | Kim | A61B 42/10 428/223 |
| 5,960,497 A | 10/1999 | Castellino et al. | |
| 6,080,168 A | 6/2000 | Levin et al. | |
| 6,086,591 A | 7/2000 | Bojarski | |
| 6,142,982 A | 11/2000 | Hunt et al. | |
| 6,471,715 B1 | 10/2002 | Weiss | |
| 6,500,112 B1 | 12/2002 | Khouri | |
| 6,553,998 B2 | 4/2003 | Heaton et al. | |
| 6,641,575 B1 | 11/2003 | Lonky | |
| 6,685,681 B2 | 2/2004 | Lockwood et al. | |
| 6,695,823 B1 | 2/2004 | Lina et al. | |
| 6,712,830 B2 | 3/2004 | Esplin | |
| 6,767,334 B1 | 7/2004 | Randolph | |
| 6,770,794 B2 | 8/2004 | Fleischmann | |
| 6,814,079 B2 | 11/2004 | Heaton et al. | |
| 6,893,452 B2 | 5/2005 | Jacobs | |
| 6,936,037 B2 | 8/2005 | Bubb et al. | |
| 6,951,553 B2 | 10/2005 | Bubb et al. | |
| 6,994,702 B1 | 2/2006 | Johnson | |
| 7,004,915 B2 | 2/2006 | Boynton et al. | |
| 7,025,755 B2 | 4/2006 | Epstein | |
| 7,070,584 B2 | 7/2006 | Johnson et al. | |
| 7,117,869 B2 | 10/2006 | Heaton et al. | |
| 7,128,735 B2 | 10/2006 | Weston | |
| 7,144,390 B1 | 12/2006 | Hannigan et al. | |
| 7,153,312 B1 | 12/2006 | Torrie et al. | |
| 7,156,862 B2 | 1/2007 | Jacobs et al. | |
| 7,172,615 B2 | 2/2007 | Morriss et al. | |
| 7,189,238 B2 | 3/2007 | Lombardo et al. | |
| 7,196,054 B1 | 3/2007 | Drohan et al. | |
| 7,198,046 B1 | 4/2007 | Argenta et al. | |
| 7,216,651 B2 | 5/2007 | Argenta et al. | |
| D544,092 S | 6/2007 | Lewis | |
| 7,262,174 B2 | 8/2007 | Jiang et al. | |
| 7,279,612 B1 | 10/2007 | Heaton et al. | |
| 7,315,183 B2 | 1/2008 | Hinterscher | |
| 7,351,250 B2 | 4/2008 | Zamierowski | |
| 7,361,184 B2 | 4/2008 | Joshi | |
| 7,367,342 B2 | 5/2008 | Butler | |
| 7,381,211 B2 | 6/2008 | Zamierowski | |
| 7,381,859 B2 | 6/2008 | Hunt et al. | |
| 7,413,571 B2 | 8/2008 | Zamierowski | |
| 7,438,705 B2 | 10/2008 | Karpowicz et al. | |
| 7,494,482 B2 | 2/2009 | Orgill et al. | |
| 7,534,240 B1 | 5/2009 | Johnson | |
| 7,540,848 B2 | 6/2009 | Hannigan et al. | |
| 7,553,306 B1 | 6/2009 | Hunt et al. | |
| 7,553,923 B2 | 6/2009 | Williams et al. | |
| 7,569,742 B2 | 8/2009 | Haggstrom et al. | |
| 7,578,532 B2 | 8/2009 | Schiebler | |
| D602,583 S | 10/2009 | Pidgeon et al. | |
| 7,611,500 B1 | 11/2009 | Lina et al. | |
| 7,615,036 B2 | 11/2009 | Joshi et al. | |
| 7,618,382 B2 | 11/2009 | Vogel et al. | |
| 7,625,362 B2 | 12/2009 | Boehringer et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,683,667 B2 | 3/2010 | Kim | |
| 7,699,823 B2 | 4/2010 | Haggstrom et al. | |
| 7,699,830 B2 | 4/2010 | Martin | |
| 7,699,831 B2 | 4/2010 | Bengtson et al. | |
| 7,700,819 B2 | 4/2010 | Ambrosio et al. | |
| 7,708,724 B2 | 5/2010 | Weston | |
| 7,713,743 B2 | 5/2010 | Villanueva et al. | |
| 7,722,528 B2 | 5/2010 | Arnal et al. | |
| 7,723,560 B2 | 5/2010 | Lockwood et al. | |
| 7,754,937 B2 | 7/2010 | Boehringer et al. | |
| 7,776,028 B2 | 8/2010 | Miller et al. | |
| 7,777,522 B2 | 8/2010 | Yang et al. | |
| 7,779,625 B2 | 8/2010 | Joshi et al. | |
| D625,801 S | 10/2010 | Pidgeon et al. | |
| 7,815,616 B2 | 10/2010 | Boehringer et al. | |
| 7,820,453 B2 | 10/2010 | Heylen et al. | |
| 7,846,141 B2 | 12/2010 | Weston | |
| 7,857,806 B2 | 12/2010 | Karpowicz et al. | |
| 7,896,856 B2 | 3/2011 | Petrosenko et al. | |
| 7,909,805 B2 | 3/2011 | Weston | |
| 7,942,866 B2 | 5/2011 | Radl et al. | |
| 7,951,124 B2 | 5/2011 | Boehringer et al. | |
| 7,976,519 B2 | 7/2011 | Bubb et al. | |
| 7,981,098 B2 | 7/2011 | Boehringer et al. | |
| 8,030,534 B2 | 10/2011 | Radl et al. | |
| 8,062,272 B2 | 11/2011 | Weston | |
| 8,062,295 B2 | 11/2011 | McDevitt et al. | |
| 8,062,331 B2 | 11/2011 | Zamierowski | |
| 8,070,773 B2 | 12/2011 | Zamierowski | |
| 8,080,702 B2 | 12/2011 | Blott et al. | |
| 8,100,887 B2 | 1/2012 | Weston et al. | |
| 8,114,126 B2 | 2/2012 | Heaton et al. | |
| 8,123,781 B2 | 2/2012 | Zamierowski | |
| 8,128,615 B2 | 3/2012 | Blott et al. | |
| 8,129,580 B2 | 3/2012 | Wilkes et al. | |
| 8,142,419 B2 | 3/2012 | Heaton et al. | |
| 8,162,909 B2 | 4/2012 | Blott et al. | |
| 8,172,816 B2 | 5/2012 | Kazala, Jr. et al. | |
| 8,182,413 B2 | 5/2012 | Browning | |
| 8,187,237 B2 | 5/2012 | Seegert | |
| 8,188,331 B2 | 5/2012 | Barta et al. | |
| 8,197,467 B2 | 6/2012 | Heaton et al. | |
| 8,207,392 B2 | 6/2012 | Haggstrom et al. | |
| 8,215,929 B2 | 7/2012 | Shen et al. | |
| 8,235,955 B2 | 8/2012 | Blott et al. | |
| 8,246,590 B2 | 8/2012 | Hu et al. | |
| 8,273,105 B2 | 9/2012 | Cohen et al. | |
| 8,353,931 B2 | 1/2013 | Stopek et al. | |
| 8,376,972 B2 | 2/2013 | Fleischmann | |
| 8,399,730 B2 | 3/2013 | Kazala, Jr. et al. | |
| 8,444,392 B2 | 5/2013 | Turner et al. | |
| 8,444,611 B2 | 5/2013 | Wilkes et al. | |
| 8,447,375 B2 | 5/2013 | Shuler | |
| 8,460,255 B2 | 6/2013 | Joshi et al. | |
| 8,460,257 B2 | 6/2013 | Locke et al. | |
| 8,481,804 B2 | 7/2013 | Timothy | |
| 8,486,032 B2 | 7/2013 | Seegert et al. | |
| 8,500,704 B2 | 8/2013 | Boehringer et al. | |
| 8,500,776 B2 | 8/2013 | Ebner | |
| 8,523,832 B2 | 9/2013 | Seegert | |
| 8,535,296 B2 | 9/2013 | Blott et al. | |
| 8,562,576 B2 | 10/2013 | Hu et al. | |
| 8,608,776 B2 | 12/2013 | Coward et al. | |
| 8,622,981 B2 | 1/2014 | Hartwell et al. | |
| 8,628,505 B2 | 1/2014 | Weston | |
| 8,632,523 B2 | 1/2014 | Eriksson et al. | |
| 8,679,080 B2 | 3/2014 | Kazala, Jr. et al. | |
| 8,679,153 B2 | 3/2014 | Dennis | |
| 8,680,360 B2 | 3/2014 | Greener et al. | |

(56) References Cited

U.S. PATENT DOCUMENTS

| | | |
|---|---|---|
| 8,708,984 B2 | 4/2014 | Robinson et al. |
| 8,715,256 B2 | 5/2014 | Greener |
| 8,721,629 B2 | 5/2014 | Hardman et al. |
| 8,747,375 B2 | 6/2014 | Barta et al. |
| 8,764,732 B2 | 7/2014 | Hartwell |
| 8,791,315 B2 | 7/2014 | Lattimore et al. |
| 8,791,316 B2 | 7/2014 | Greener |
| 8,802,916 B2 | 8/2014 | Griffey et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,882,730 B2 | 11/2014 | Zimnitsky et al. |
| 8,936,618 B2 | 1/2015 | Sealy et al. |
| 8,945,030 B2 | 2/2015 | Weston |
| 8,951,235 B2 | 2/2015 | Allen et al. |
| 9,050,398 B2 | 6/2015 | Armstrong et al. |
| 9,061,095 B2 | 6/2015 | Adie et al. |
| 9,084,845 B2 | 7/2015 | Adie et al. |
| 9,180,231 B2 | 11/2015 | Greener |
| 9,220,822 B2 | 12/2015 | Hartwell |
| 9,226,737 B2 | 1/2016 | Dunn |
| 9,301,742 B2 | 4/2016 | Dunn |
| 9,421,132 B2 | 8/2016 | Dunn |
| 9,597,484 B2 | 3/2017 | Dunn |
| 2001/0029956 A1 | 10/2001 | Argenta et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0178274 A1* | 9/2003 | Chi ............... A45C 13/002 190/125 |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0243073 A1 | 12/2004 | Lockwood et al. |
| 2005/0119694 A1 | 6/2005 | Jacobs et al. |
| 2005/0182445 A1 | 8/2005 | Zamierowski |
| 2005/0209574 A1 | 9/2005 | Boehringer et al. |
| 2005/0222544 A1 | 10/2005 | Weston |
| 2005/0222613 A1 | 10/2005 | Ryan |
| 2005/0240220 A1 | 10/2005 | Zamierowski |
| 2005/0258887 A1 | 11/2005 | Ito et al. |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur |
| 2006/0135921 A1 | 6/2006 | Wiercinski et al. |
| 2006/0213527 A1 | 9/2006 | Argenta et al. |
| 2006/0257457 A1 | 11/2006 | Gorman et al. |
| 2006/0259074 A1 | 11/2006 | Kelleher et al. |
| 2007/0027475 A1* | 2/2007 | Pagedas ........... A61B 17/06166 606/228 |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0118096 A1 | 5/2007 | Smith et al. |
| 2007/0123816 A1 | 5/2007 | Zhu et al. |
| 2007/0149910 A1 | 6/2007 | Zocher |
| 2007/0185463 A1 | 8/2007 | Mulligan |
| 2007/0219513 A1 | 9/2007 | Lina et al. |
| 2007/0265585 A1 | 11/2007 | Joshi et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0103462 A1* | 5/2008 | Wenzel ............ A61M 1/0011 604/313 |
| 2008/0108977 A1 | 5/2008 | Heaton et al. |
| 2008/0167593 A1* | 7/2008 | Fleischmann ...... A61M 1/0088 602/48 |
| 2008/0177253 A1 | 7/2008 | Boehringer et al. |
| 2008/0275409 A1* | 11/2008 | Kane .............. A61F 13/00068 604/305 |
| 2008/0287973 A1 | 11/2008 | Aster et al. |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0227938 A1 | 9/2009 | Fasching et al. |
| 2009/0246238 A1 | 10/2009 | Gorman et al. |
| 2009/0259203 A1 | 10/2009 | Hu et al. |
| 2009/0299255 A1 | 12/2009 | Kazala, Jr. et al. |
| 2009/0299256 A1 | 12/2009 | Barta et al. |
| 2009/0299303 A1 | 12/2009 | Seegert |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2010/0022972 A1 | 1/2010 | Lina et al. |
| 2010/0022990 A1 | 1/2010 | Karpowicz et al. |
| 2010/0028407 A1 | 2/2010 | Del Priore et al. |
| 2010/0030132 A1 | 2/2010 | Niezgoda et al. |
| 2010/0036333 A1 | 2/2010 | Schenk, III et al. |
| 2010/0087854 A1 | 4/2010 | Stopek et al. |
| 2010/0100022 A1 | 4/2010 | Greener et al. |
| 2010/0100063 A1 | 4/2010 | Joshi et al. |
| 2010/0106184 A1 | 4/2010 | Coward et al. |
| 2010/0121286 A1 | 5/2010 | Locke et al. |
| 2010/0121287 A1 | 5/2010 | Smith et al. |
| 2010/0137775 A1 | 6/2010 | Hu et al. |
| 2010/0137890 A1 | 6/2010 | Martinez et al. |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0211030 A1 | 8/2010 | Turner et al. |
| 2010/0256672 A1 | 10/2010 | Weinberg et al. |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0305490 A1 | 12/2010 | Coulthard et al. |
| 2010/0318046 A1 | 12/2010 | Boehringer et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0054283 A1 | 3/2011 | Shuler |
| 2011/0054365 A1 | 3/2011 | Greener |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0105963 A1 | 5/2011 | Hu et al. |
| 2011/0106026 A1 | 5/2011 | Wu et al. |
| 2011/0113559 A1* | 5/2011 | Dodd ............... B64D 11/0647 5/690 |
| 2011/0130774 A1 | 6/2011 | Criscuolo et al. |
| 2011/0172760 A1 | 7/2011 | Anderson |
| 2011/0178451 A1 | 7/2011 | Robinson et al. |
| 2011/0213287 A1 | 9/2011 | Lattimore et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |

(56) References Cited

U.S. PATENT DOCUMENTS

| | | |
|---|---|---|
| 2011/0245788 A1 | 10/2011 | Marquez Canada |
| 2011/0264138 A1 | 10/2011 | Avelar et al. |
| 2011/0270201 A1 | 11/2011 | Bubb et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0313374 A1 | 12/2011 | Lockwood et al. |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Coulthard et al. |
| 2012/0029449 A1 | 2/2012 | Khosrowshahi |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0073736 A1* | 3/2012 | O'Connor ............... B29C 43/28 156/243 |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |
| 2012/0123358 A1 | 5/2012 | Hall et al. |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | Du Plessis et al. |
| 2012/0150078 A1 | 6/2012 | Chen et al. |
| 2012/0150133 A1 | 6/2012 | Heaton et al. |
| 2012/0157942 A1 | 6/2012 | Weston |
| 2012/0165764 A1 | 6/2012 | Allen et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1 | 8/2012 | Dunn |
| 2012/0220968 A1 | 8/2012 | Confalone et al. |
| 2012/0222687 A1 | 9/2012 | Czajka, Jr. et al. |
| 2012/0277773 A1 | 11/2012 | Sargeant et al. |
| 2012/0302440 A1 | 11/2012 | Theliander et al. |
| 2013/0096518 A1 | 4/2013 | Hall et al. |
| 2013/0110058 A1 | 5/2013 | Adie et al. |
| 2013/0131564 A1 | 5/2013 | Locke et al. |
| 2013/0138054 A1 | 5/2013 | Fleischmann |
| 2013/0150814 A1 | 6/2013 | Buan |
| 2013/0197457 A1 | 8/2013 | Kazala, Jr. et al. |
| 2013/0245527 A1 | 9/2013 | Croizat et al. |
| 2013/0253401 A1 | 9/2013 | Locke et al. |
| 2013/0274717 A1 | 10/2013 | Dunn |
| 2013/0310781 A1 | 11/2013 | Phillips et al. |
| 2013/0317465 A1 | 11/2013 | Seegert |
| 2013/0331757 A1 | 12/2013 | Belson |
| 2014/0066868 A1 | 3/2014 | Freedman et al. |
| 2014/0068914 A1 | 3/2014 | Coward et al. |
| 2014/0088455 A1 | 3/2014 | Christensen et al. |
| 2014/0094730 A1 | 4/2014 | Greener et al. |
| 2014/0180225 A1 | 6/2014 | Dunn |
| 2014/0194836 A1 | 7/2014 | Kazala, Jr. et al. |
| 2014/0194837 A1 | 7/2014 | Robinson et al. |
| 2014/0213994 A1 | 7/2014 | Hardman et al. |
| 2014/0228789 A1 | 8/2014 | Wilkes et al. |
| 2014/0336602 A1 | 11/2014 | Karpowicz et al. |
| 2014/0343517 A1 | 11/2014 | Jameson |
| 2015/0000018 A1* | 1/2015 | Brandt ............... A41D 13/0156 2/455 |
| 2015/0005722 A1 | 1/2015 | Hu et al. |
| 2015/0025484 A1 | 1/2015 | Simmons et al. |
| 2015/0065968 A1 | 3/2015 | Sealy et al. |
| 2015/0075697 A1* | 3/2015 | Gildersleeve ..... A61F 13/00038 156/60 |
| 2015/0080947 A1 | 3/2015 | Greener |
| 2015/0112290 A1 | 4/2015 | Dunn |
| 2015/0112311 A1 | 4/2015 | Hammond et al. |
| 2015/0119865 A1 | 4/2015 | Barta et al. |
| 2015/0148760 A1 | 5/2015 | Dodd et al. |
| 2015/0150729 A1 | 6/2015 | Dagger et al. |
| 2015/0159066 A1 | 6/2015 | Hartwell et al. |
| 2015/0164174 A1* | 6/2015 | West ..................... A42B 3/069 2/414 |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0320602 A1 | 11/2015 | Locke et al. |
| 2016/0067939 A1* | 3/2016 | Liebe ................ A61F 13/00034 428/35.7 |
| 2016/0278773 A1 | 9/2016 | Dunn |
| 2016/0287765 A1* | 10/2016 | Canner ............... A61M 1/0088 |
| 2016/0354086 A1 | 12/2016 | Dunn |
| 2017/0165116 A1 | 6/2017 | Dunn |
| 2019/0231944 A1* | 8/2019 | Dunn ................. A61F 13/0216 |

FOREIGN PATENT DOCUMENTS

| | | |
|---|---|---|
| DE | 2949920 A1 | 3/1981 |
| DE | 102012001752 A1 | 8/2013 |
| EP | 1320342 A1 | 6/2003 |
| EP | 2094211 A1 | 9/2009 |
| EP | 2279016 A1 | 2/2011 |
| EP | 2341955 A1 | 7/2011 |
| EP | 2366721 A1 | 9/2011 |
| EP | 2367517 A2 | 9/2011 |
| EP | 2368523 A1 | 9/2011 |
| EP | 2404571 A1 | 1/2012 |
| EP | 2404626 A2 | 1/2012 |
| EP | 2563421 A1 | 3/2013 |
| EP | 2567717 A1 | 3/2013 |
| EP | 2594299 A2 | 5/2013 |
| EP | 2601984 A2 | 6/2013 |
| EP | 2623137 A2 | 8/2013 |
| GB | 2389794 A | 12/2003 |
| GB | 2423019 A | 8/2006 |
| GB | 2496310 B | 5/2013 |
| IE | 20140129 A1 | 3/2016 |
| WO | 200189392 A2 | 11/2001 |
| WO | 2002/05737 A1 | 1/2002 |
| WO | 2003/003948 A1 | 1/2003 |
| WO | 2004/018020 A1 | 3/2004 |
| WO | 2006/041496 A1 | 4/2006 |
| WO | 2006/046060 A2 | 5/2006 |
| WO | 2006087021 A1 | 8/2006 |
| WO | 2008/064502 A1 | 6/2008 |
| WO | 2008/104609 A1 | 9/2008 |
| WO | 2009/019495 A1 | 2/2009 |
| WO | 2009/071926 A1 | 6/2009 |
| WO | 2009/071933 A2 | 6/2009 |
| WO | 2009/112062 A1 | 9/2009 |
| WO | 2009/112848 A1 | 9/2009 |
| WO | 2009/114624 A2 | 9/2009 |
| WO | 2009/156709 A1 | 12/2009 |
| WO | 2009158125 A1 | 12/2009 |
| WO | 2010/033725 A2 | 3/2010 |
| WO | 2010/059612 A2 | 5/2010 |
| WO | 2010/075180 A2 | 7/2010 |
| WO | 2010/078349 A2 | 7/2010 |
| WO | 2010/079359 A1 | 7/2010 |
| WO | 2010/092334 A1 | 8/2010 |
| WO | 2010/097570 A1 | 9/2010 |
| WO | 2011/023384 A1 | 3/2011 |
| WO | 2011/087871 A2 | 7/2011 |
| WO | 2011/091169 A1 | 7/2011 |
| WO | 2011/106722 A1 | 9/2011 |
| WO | 2011/115908 A1 | 9/2011 |
| WO | 2011/135286 A1 | 11/2011 |
| WO | 2011/135287 A1 | 11/2011 |
| WO | 2011/137230 A1 | 11/2011 |
| WO | 2012/021553 A1 | 2/2012 |
| WO | 2012/038727 A2 | 3/2012 |

(56) References Cited

FOREIGN PATENT DOCUMENTS

| | | |
|---|---|---|
| WO | 2012/082716 A2 | 6/2012 |
| WO | 2012/082876 A1 | 6/2012 |
| WO | 2012/087376 A1 | 6/2012 |
| WO | 2012/106590 A2 | 8/2012 |
| WO | 2012/112204 A1 | 8/2012 |
| WO | 2012/136707 A1 | 10/2012 |
| WO | 2012142473 A1 | 10/2012 |
| WO | 2012/156655 A1 | 11/2012 |
| WO | 2012/168678 A1 | 12/2012 |
| WO | 2013/012381 A1 | 1/2013 |
| WO | 2013007973 A2 | 1/2013 |
| WO | 2013/043258 A1 | 3/2013 |
| WO | 2013/071243 A2 | 5/2013 |
| WO | 2013/074829 A1 | 5/2013 |
| WO | 2013079947 A1 | 6/2013 |
| WO | 2013/175309 A1 | 11/2013 |
| WO | 2013/175310 A1 | 11/2013 |
| WO | 2014/013348 A2 | 1/2014 |
| WO | 2014/014842 A1 | 1/2014 |
| WO | 2014/014871 A1 | 1/2014 |
| WO | 2014/014922 A1 | 1/2014 |
| WO | 2014024048 A1 | 2/2014 |
| WO | 2014140578 A1 | 9/2014 |
| WO | 2014/158526 A1 | 10/2014 |
| WO | 2014/165275 A1 | 10/2014 |
| WO | 2015008054 A1 | 1/2015 |
| WO | 2015061352 A2 | 4/2015 |
| WO | 2015109359 A1 | 7/2015 |
| WO | 2015110409 A1 | 7/2015 |
| WO | 2015110410 A1 | 7/2015 |
| WO | 2016/184913 A1 | 11/2016 |
| WO | 2017/063036 A1 | 4/2017 |

OTHER PUBLICATIONS

Bengezi et al., Elevation as a treatment for fasciotomy wound closure. Can J Plast Surg. 2013 Fall;21(3):192-4.

Jauregui et al., Fasciotomy closure techniques. J Orthop Surg (Hong Kong). Jan. 2017;25(1):2309499016684724. 8 pages.

Epstein et al., Lipoabdominoplasty Without Drains or Progressive Tension Sutures: An Analysis of 100 Consecutive Patients. Aesthetic Surgery Journal. Apr. 2015;35(4):434-440.

Hougaard et al., The open abdomen: temporary closure with a modified negative pressure therapy technique. Int Wound J. Jun. 2014;11 Suppl 1:13-6.

International Preliminary Report on Patentability by the International Bureau of WIPO for International Patent Application No. PCT/US2016/067051 dated Jun. 19, 2018.

Kapischke et al., Self-fixating mesh for the Lichtenstein procedure—a prestudy. Langenbecks Arch Surg. Apr. 2010;395(4):317-22.

Macias et al., Decrease in Seroma Rate After Adopting Progressive Tension Sutures Without Drains: A Single Surgery Center Experience of 451 Abdominoplasties over 7 Years. Aesthetic Surgery Journal. Mar. 2016;36(9):1029-1035.

Pollock et al., Progressive Tension Sutures in Abdominoplasty: A Review of 597 Consecutive Cases. Aesthetic Surgery Journal. Aug. 2012;32(6):729-742.

Quaba et al., The no-drain, no-quilt abdominoplasty: a single-surgeon series of 271 patients. Plast Reconstr Surg. Mar. 2015;135(3):751-60.

Rothenberg et al., Emerging Insights on Closed Incision NPWT and Transmetatarsal Amputations. http://www.podiatrytoday.com/emerging-insights-closed-incision-npwt-and-transmetatarsal-amputations. Apr. 2015;28(4):1-5.

International Search Report and Written Opinion for Application No. PCT/US2018/038851, dated Jan. 15, 2019, 19 pages.

Supplementary European Search Report for Application No. 16876731.7, dated May 7, 2019, 8 pages.

* cited by examiner

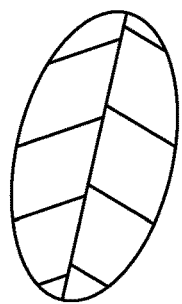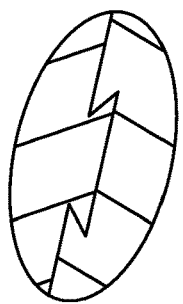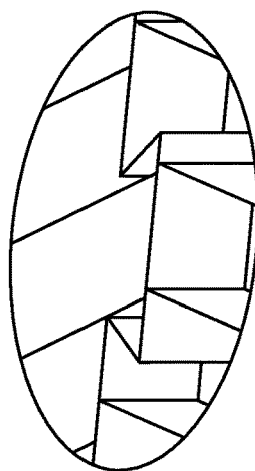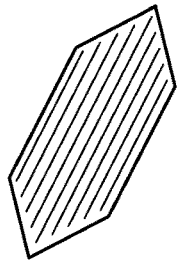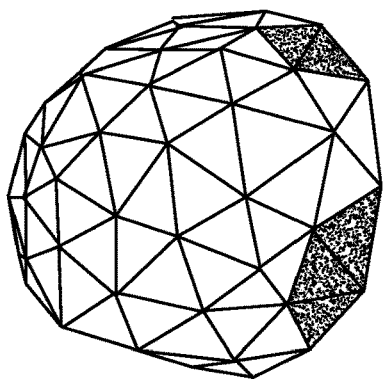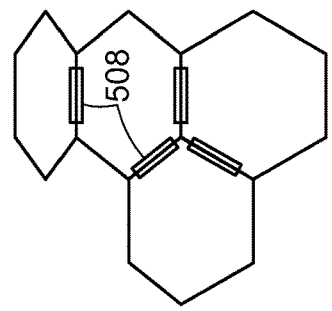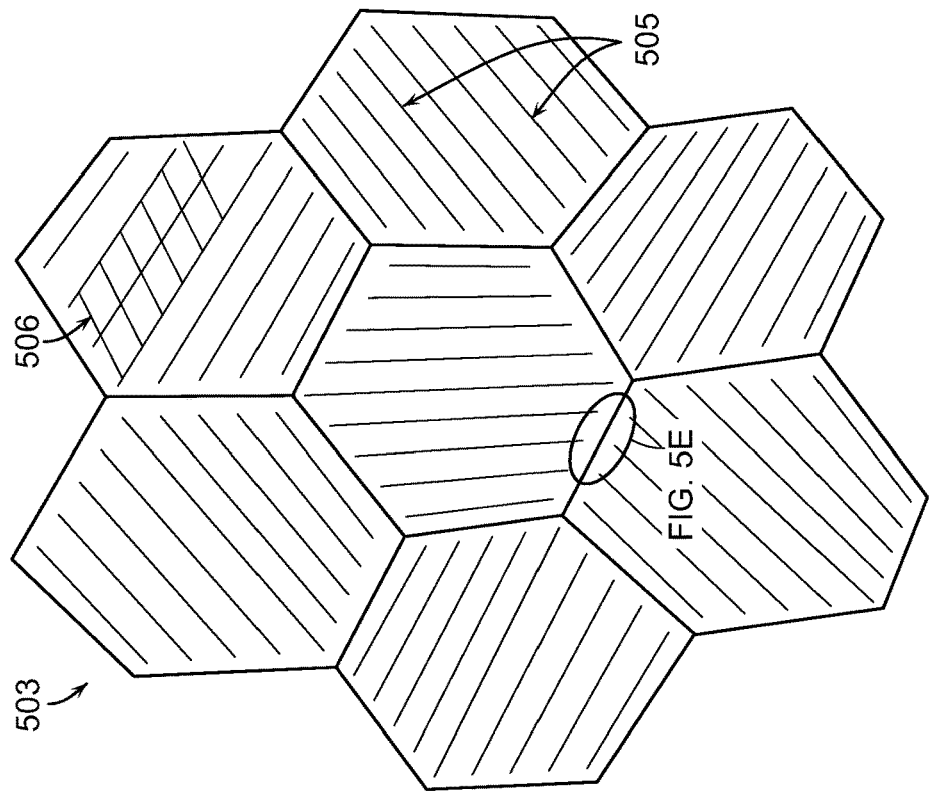

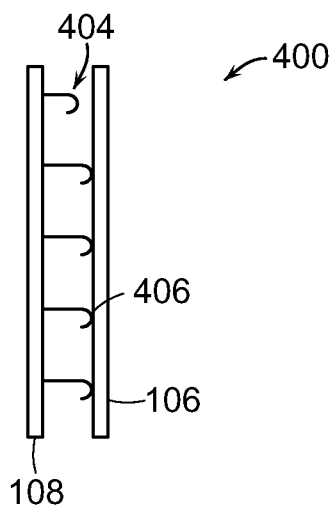
FIG. 9
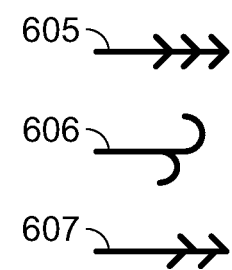
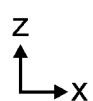
FIG. 10

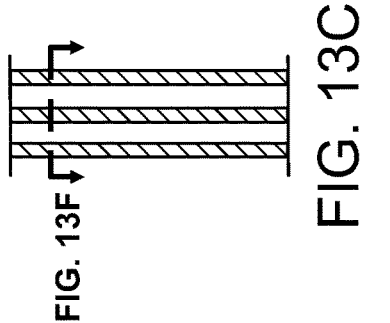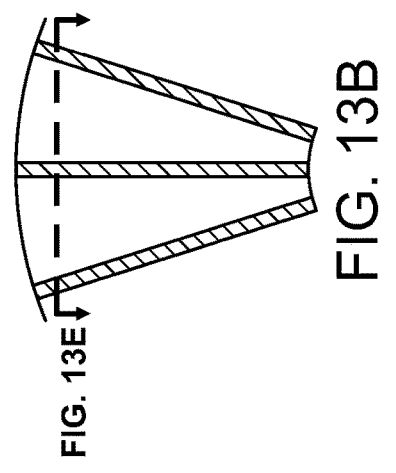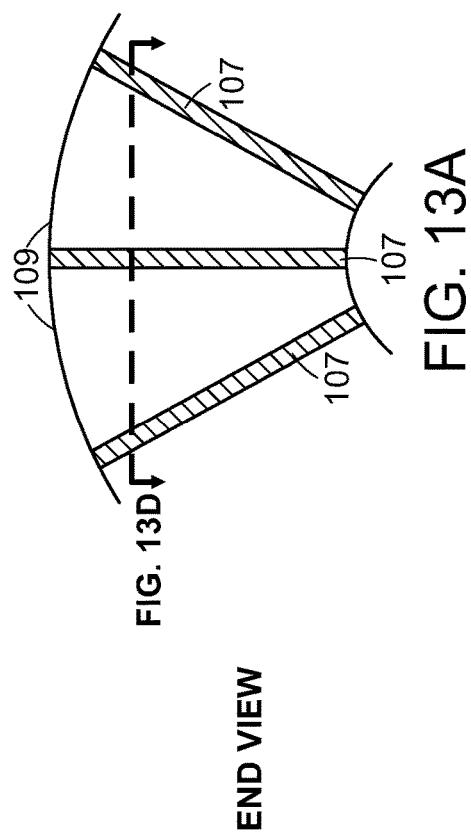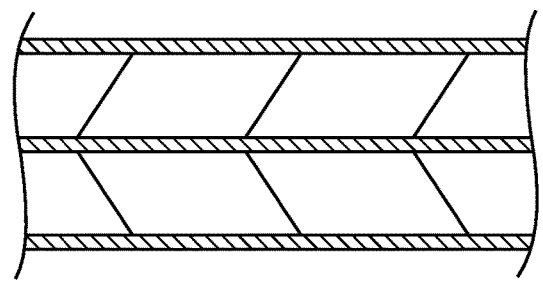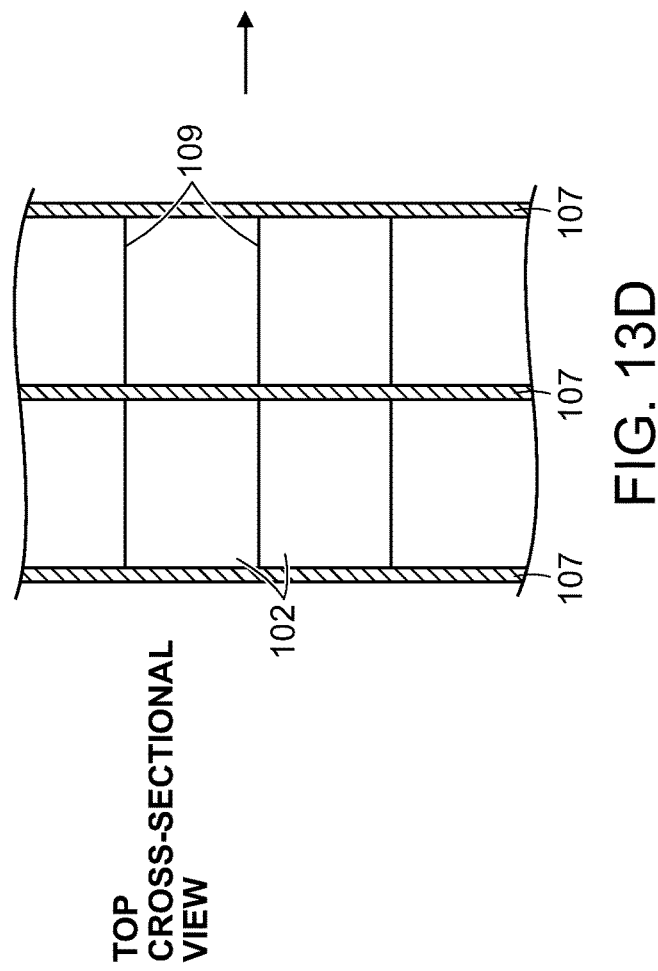

1200

```
┌─────────────────────────────────────────────────────┐
│ Surgically preparing an open wound, such as an      │
│ amputation wound, at a body region, such as an      │
│ amputated limb, for negative pressure wound closure │
│ therapy, the open wound having a depth including    │
│ a deep portion and a shallow portion                │
│ 1202                                                │
└─────────────────────────────────────────────────────┘
                          │
                          ▼
┌─────────────────────────────────────────────────────┐
│ Configuring a wound closure device including a      │
│ collapsible compression structure for the wound     │
│ opening, the configured wound closure device having │
│ a size and shape conforming to the wound opening    │
│ 1204                                                │
└─────────────────────────────────────────────────────┘
                          │
                          ▼
┌─────────────────────────────────────────────────────┐
│ Placing the wound closure device over the open wound│
│ 1206                                                │
└─────────────────────────────────────────────────────┘
                          │
                          ▼
┌─────────────────────────────────────────────────────┐
│ Applying a negative pressure at a port or inlet to  │
│ cause the compression structure to at least partly  │
│ collapse, the collapse of the compression structure │
│ causing the deep portion of the wound margins to    │
│ close before the shallow portion.                   │
│ 1208                                                │
└─────────────────────────────────────────────────────┘
                          │
                          ▼
┌─────────────────────────────────────────────────────┐
│ Optionally, removing the wound closure device and   │
│ applying a second wound closure device to the wound │
│ 1210                                                │
└─────────────────────────────────────────────────────┘
                          │
                          ▼
┌─────────────────────────────────────────────────────┐
│ Removing the wound closure device and completing    │
│ wound closure with, or without, sutures             │
│ 1212                                                │
└─────────────────────────────────────────────────────┘
```

```
┌─────────────────────────────────────────────────────────────┐
│ Surgically preparing a wound in a tissue that has a depth   │
│ including a deep portion and a shallow portion for negative │
│              pressure wound closure therapy                 │
│                            1402                             │
└─────────────────────────────────────────────────────────────┘
                              ↓
┌─────────────────────────────────────────────────────────────┐
│ Configuring a wound closure device including a collapsible  │
│ structure, flaps, and a port or inlet, the collapsible      │
│ structure having a radius of curvature and, optionally,     │
│ placing a surgical drain device into the wound.             │
│                            1404                             │
└─────────────────────────────────────────────────────────────┘
                              ↓
┌─────────────────────────────────────────────────────────────┐
│ Placing the wound closure device over the wound in the      │
│ tissue, a surface of the tissue surrounding the wound       │
│ defining a radius of curvature that is greater than the     │
│ radius of curvature of the collapsible structure.           │
│                            1406                             │
└─────────────────────────────────────────────────────────────┘
                              ↓
┌─────────────────────────────────────────────────────────────┐
│ Optionally compressing the tissue on the opposite sides of  │
│ the wound while the wound closure device is attached to     │
│ tissue surfaces surrounding the wound                       │
│                            1408                             │
└─────────────────────────────────────────────────────────────┘
                              ↓
┌─────────────────────────────────────────────────────────────┐
│ Applying a negative pressure at the inlet to cause the      │
│ collapsible structure to at least partly collapse, the      │
│ collapse of the collapsible structure causing the deep      │
│ portion of the wound to close before the shallow portion.   │
│                            1410                             │
└─────────────────────────────────────────────────────────────┘
                              ↓
┌─────────────────────────────────────────────────────────────┐
│ Draining the wound of fluids during movement of the wound   │
│ margins                                                     │
│                            1412                             │
└─────────────────────────────────────────────────────────────┘
                              ↓
┌─────────────────────────────────────────────────────────────┐
│ Removing the wound closure device from the wound and        │
│ closing the wound with or without sutures                   │
│                            1414                             │
└─────────────────────────────────────────────────────────────┘
```

```
┌─────────────────────────────────────────────────────────────┐
│ Surgically preparing a wound in a tissue that includes an   │
│ undermined portion and a surface portion for negative       │
│ pressure wound closure therapy                              │
│                           1502                              │
└─────────────────────────────────────────────────────────────┘
                              │
                              ▼
┌─────────────────────────────────────────────────────────────┐
│ Configuring a wound closure device including a compression  │
│ device such as a bladder, a drainage element, and a port or │
│ inlet.                                                      │
│                           1504                              │
└─────────────────────────────────────────────────────────────┘
                              │
                              ▼
┌─────────────────────────────────────────────────────────────┐
│           Placing the wound closure device into the wound.  │
│                           1506                              │
└─────────────────────────────────────────────────────────────┘
                              │
                              ▼
┌─────────────────────────────────────────────────────────────┐
│ Applying a negative pressure at the inlet to cause the      │
│ bladder to exert pressure on a surface of the tissue, the   │
│ pressure exerted by the bladder causing the undermined      │
│ portion of the wound to close before the surface portion.   │
│                           1508                              │
└─────────────────────────────────────────────────────────────┘
                              │
                              ▼
┌─────────────────────────────────────────────────────────────┐
│ Draining the wound of fluids through the drainage element   │
│ during movement of the wound margins.                       │
│                           1510                              │
└─────────────────────────────────────────────────────────────┘
                              │
                              ▼
┌─────────────────────────────────────────────────────────────┐
│ Removing the wound closure device from the wound and        │
│ closing the wound with or without sutures                   │
│                           1512                              │
└─────────────────────────────────────────────────────────────┘
```

```
┌─────────────────────────────────────────────────┐
│ Surgically preparing a wound in a tissue that   │
│ includes an undermined portion and a surface    │
│ portion for negative pressure wound closure     │
│ therapy                                         │
│ 1702                                            │
└─────────────────────────────────────────────────┘
```

```
┌─────────────────────────────────────────────────┐
│ Configuring a wound closure device including a  │
│ compression device such as a bladder, a         │
│ drainage element, and a port or inlet, the      │
│ drainage element being collapsible in the       │
│ horizontal and vertical directions.             │
│ 1704                                            │
└─────────────────────────────────────────────────┘
```

```
┌─────────────────────────────────────────────────┐
│ Configuring a surgical drain device.            │
│ 1706                                            │
└─────────────────────────────────────────────────┘
```

```
┌─────────────────────────────────────────────────┐
│ Placing the surgical drain device and the wound │
│ closure device into the wound, the surgical     │
│ drain device being placed ahead of the wound    │
│ closure device and wherein the surgical drain   │
│ device and wound closure device are in contact  │
│ after placement.                                │
│ 1708                                            │
└─────────────────────────────────────────────────┘
```

```
┌─────────────────────────────────────────────────┐
│ Applying a negative pressure at the inlet to    │
│ cause the compression device to exert pressure  │
│ on the wound and a surface of the tissue        │
│ surrounding the wound, the pressure exerted by  │
│ the compression device collapsing the drainage  │
│ element of the wound closure device in the      │
│ vertical and horizontal directions to           │
│ approximate wound margins in the undermined     │
│ portion and wound margins at the surface        │
│ portion, respectively.                          │
│ 1710                                            │
└─────────────────────────────────────────────────┘
```

```
┌─────────────────────────────────────────────────┐
│ Draining the wound of fluids during movement of │
│ the wound margins.                              │
│ 1712                                            │
└─────────────────────────────────────────────────┘
```

```
┌─────────────────────────────────────────────────┐
│ Removing the wound closure device from the      │
│ wound and closing the wound with or without     │
│ sutures wherein a portion of the surgical drain │
│ device remains in the closed wound              │
│ 1714                                            │
└─────────────────────────────────────────────────┘
```

FIG. 20

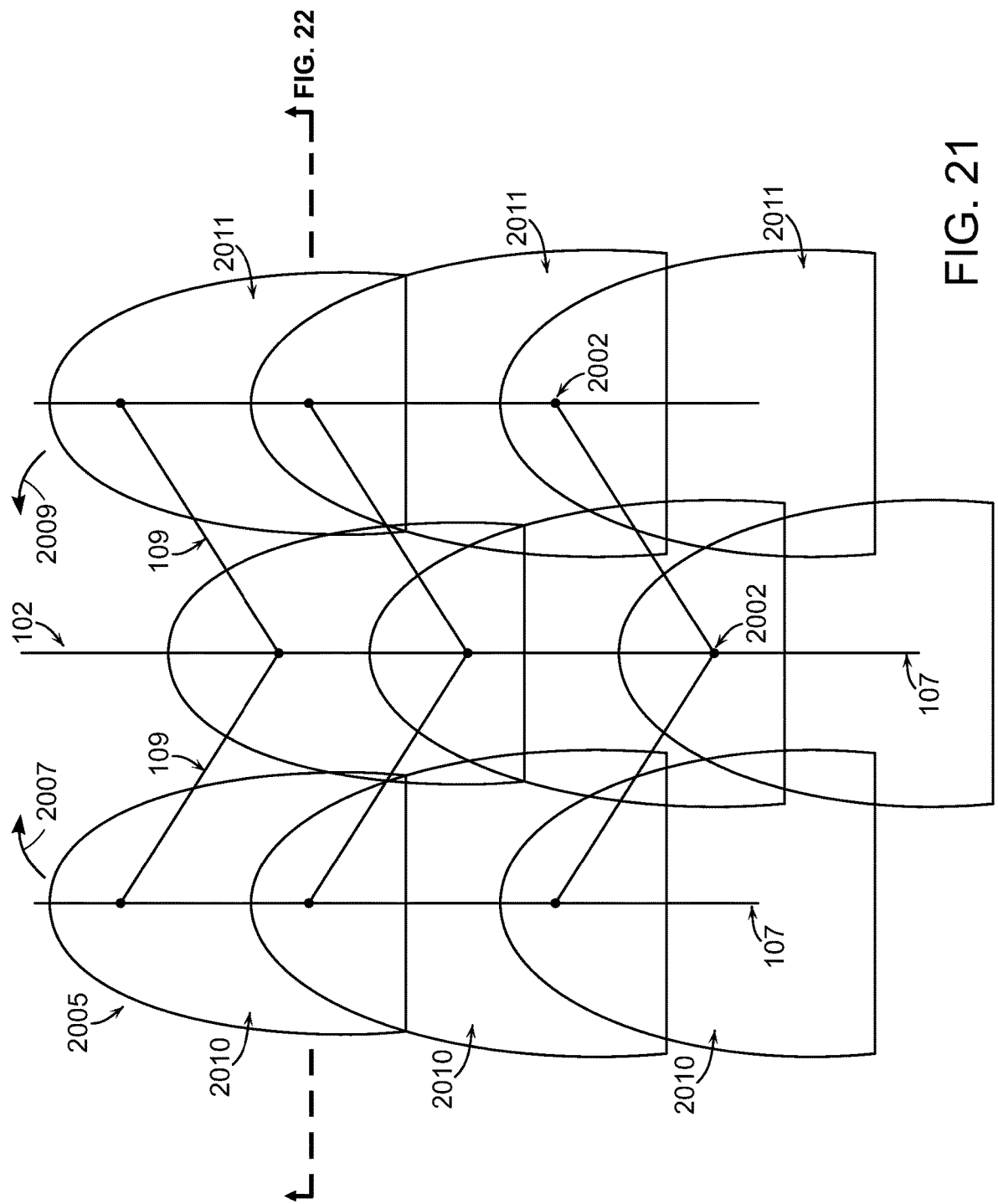

NEGATIVE PRESSURE WOUND CLOSURE DEVICES AND METHODS

RELATED APPLICATIONS

This application is a continuation-in-part of International Patent Application No. PCT/US2016/067051, filed Dec. 15, 2016, which is a continuation-in-part of U.S. patent application Ser. No. 15/066,527, filed Mar. 10, 2016, and claims priority to U.S. Provisional Patent Application 62/267,728, filed Dec. 15, 2015, the contents of the above applications being incorporated herein by reference in their entirety.

BACKGROUND OF THE INVENTION

A variety of wounds are now being treated using negative pressure wound therapy. However, many of these wounds have characteristics that limit the effectiveness of existing techniques. Wound dehiscence, in which the wound margins have substantial separation, pose significant problems in reapproximation of tissue and wound drainage. For example, there are a large number of patients undergoing amputations in the United States every year. These have different causes including traumatic injury, peripheral vascular disease, diabetes mellitus and chronic venous insufficiency. Patients with diabetic conditions, for example, often suffer from restricted blood flow that can lead to tissue necrosis at the body extremities. For patients with severe symptoms, a transmetatarsal amputation (TMA) may be recommended to remove afflicted tissue while still salvaging a portion of the foot. In many cases, a transtibial or below-knee amputation (BKA) must be performed. An important factor in the recovery of a patient from amputation is how quickly the wound can be closed. Because the gap between tissue margins can be large, the wound is manually closed by suturing. There must be ongoing attention to prevent complications such as infection, wound dehiscence, and/or ischemia. The use of an immediate post-operative prosthesis (IPOP) is commonly employed to reduce the recovery period for BKA procedures, for example.

Other examples of wounds that can be difficult to achieve approximation of the wound margins can include ulcers in which the wound opening is surrounded by tissue overlying a cavity. The undermining of the tissue surrounding the wound opening can often present problems in drainage and rapid wound closure. There are also open wounds that can occur in both the extremities and the abdominal regions in which the wound margins must rotate over a substantial distance, often up to several centimeters or more, to achieve approximation of the margins. Thus a continuing need exists for improvements in wound closure devices and methods.

SUMMARY OF THE INVENTION

This disclosure relates to embodiments of negative pressure wound closure devices, systems, and methods for wounds resulting from amputation or other open wounds having non-aligned wound margins. In preferred embodiments, the system includes a negative pressure source and a collapsing structure that is placed on the wound to provide directed preferential closure. The collapsing structure can include embodiments in which a compressive force is imparted to tissue surrounding the wound or to tissue on the sides of a wound opening with a compression wound closure device that is operative to assist in the closure of a wound cavity. Thus, the collapsing structure can include, be attached to, or operate in conjunction with, a compression structure that operates to apply a force to the tissue adjoining an open wound to move a wound margin to a more closed position. In a preferred embodiment, a collapsing compression structure includes a number of cells separated by rigid or semi-rigid membranes that are hinged together at joints. In a preferred embodiment of the compression wound closure device, the structure changes conformation during a procedure to facilitate closure of the wound. The structure, in combination with the application of negative pressure, exerts a force to the wound to facilitate closure of the wound from the deepest internal point. The structure can be rigid, or alternatively, be pre-stressed to exert a compression force on the wound to more quickly bring the wound margins together.

Preferred embodiments of wound closure devices described herein can include scale elements that enable collapse of structures within an open wound and/or above the wound. The scales can comprise a detached collapsible layer, or can comprise discrete elements mounted to an overlying collapsing structure. The scale elements can have different shapes and sizes, such as circular or combinations of curved and flat edges, operative to interact with adjacent elements that enable collapse of the connected structures and provide fluid flow through the structure during application of negative pressure. The scale elements can have one or more rounded edges to facilitate sliding relative to tissue during placement and/or operation. The scale elements can have surfaces and/or edges that have a convex or concave shape. The scale elements can have shapes that generally conform to the arcuate shape of the wound or tissue surfaces contacting the scale elements. Thus, as the collapsing structure moves along an arcuate path, the scale elements move to facilitate an efficient movement of the structure which provides for closure of the wound margins. The arcuate shape can extend along one axis, such as a cylindrical shaped path or along two arcuate paths as in a domed structure. Alternatively, the scale elements can be curved or flat and sized to enable collapse without overlapping adjacent scale elements, scale elements can also include elastic elements or covering to enable movement and reducing friction with the tissue surfaces. The smaller sized scales are consequently spaced apart during wound closure but can abut one another after collapse. Note that a collapsing structure can comprise a single unit that is both positioned in the wound and above the wound.

The device can be used without any sutures in cases where the skin on opposite sides of the wound is sufficiently aligned. Alternatively, sutures can be used to provide alignment in the case of a wound where the margins and/or the overlying skin are not well aligned or are not amenable to restructuring to make them so aligned.

Wound closure of open wounds in which the wound margins are not substantially parallel can include the amputation of limbs or other regions of the body having substantially curved contoured regions. Wound closure devices fitting over and/or within the wound can require an arcuate shape to be effective to close such wounds. Often different depths within the wound will close at different rates upon the application of negative pressure. It is critical to provide arcuately shaped devices that are effective to close the deeper portions of the wound margins in advance of the shallower portions to avoid the creation of separated wound margin regions that are not visible.

Wound closure devices in accordance with the invention can include one or more device components that are inserted within the wound to facilitate wound closure. A preferred embodiment can employ a double sided anchoring matrix that is inserted in all or a portion of the wound that will attach to both wound margins. The matrix can have apertures extending through the matrix to facilitate wound margin contact through the apertures. One or both sides of the matrix can have tissue anchors to grasp the margin surfaces. Adhesive material can also be used as a tissue anchor material. The matrix can comprise a bio-absorbable material that does not need to be removed from the wound upon wound closure. A further preferred embodiment uses an arcuately shaped closure device in which an outer portion has a larger dimension then an inner portion as the outer portion has a substantially greater length upon insertion into the wound.

In another preferred embodiment for treating an open wound, a common problem involves the drainage and closure of ulcerative conditions. A collapsing structure using negative pressure around therapy and a compression device that is operative to apply a force to the tissue surrounding the wound can also be used to facilitate wound closure. This procedure can also be used with or without sutures to close the wound.

BRIEF DESCRIPTION OF THE DRAWINGS

FIG. 5A illustrates exemplary compression structures and cell shapes in accordance with various aspects and embodiments of the present invention.

FIG. 5B illustrates a single cell shape of the structure shown in FIG. 5A under compression.

FIGS. 5C and 5D illustrate three-dimensional representations of exemplary compression structures in accordance with various embodiments of the present invention.

FIGS. 5E and 5F illustrate top views of collapse of a wall of a cell in a compression structure according to various embodiments of the present invention.

FIG. 5G illustrates a perspective view of collapse of a wall of a cell in a compression structure according to various embodiments of the present invention.

FIG. 9 illustrates an example anchoring system included in a wound closure device in accordance with various embodiments of the present invention.

FIG. 10 illustrates several grasping features for an anchoring system in accordance with embodiments of the present invention.

FIGS. 13A-13C illustrate end views of progressive steps of an exemplary compression structure during compression in accordance with various embodiments of the present invention.

FIGS. 13D-13F illustrate cross-sectional top views corresponding to the end views of FIGS. 13A-13C, respectively.

FIG. 17 illustrates a methodology for wound healing and closure in accordance with various embodiments of the present invention.

FIG. 18 illustrates a methodology for wound healing and closure in accordance with various embodiments of the present invention.

FIG. 19 illustrates a methodology for wound healing and closure in accordance with various embodiments of the present invention.

FIG. 20 illustrates a methodology for wound healing and closure in accordance with various embodiments of the present invention.

FIG. 21 illustrates a portion of a collapsible structure including a scale system in accordance with various embodiments of the present invention.

DETAILED DESCRIPTION OF THE INVENTION

Figure 1:
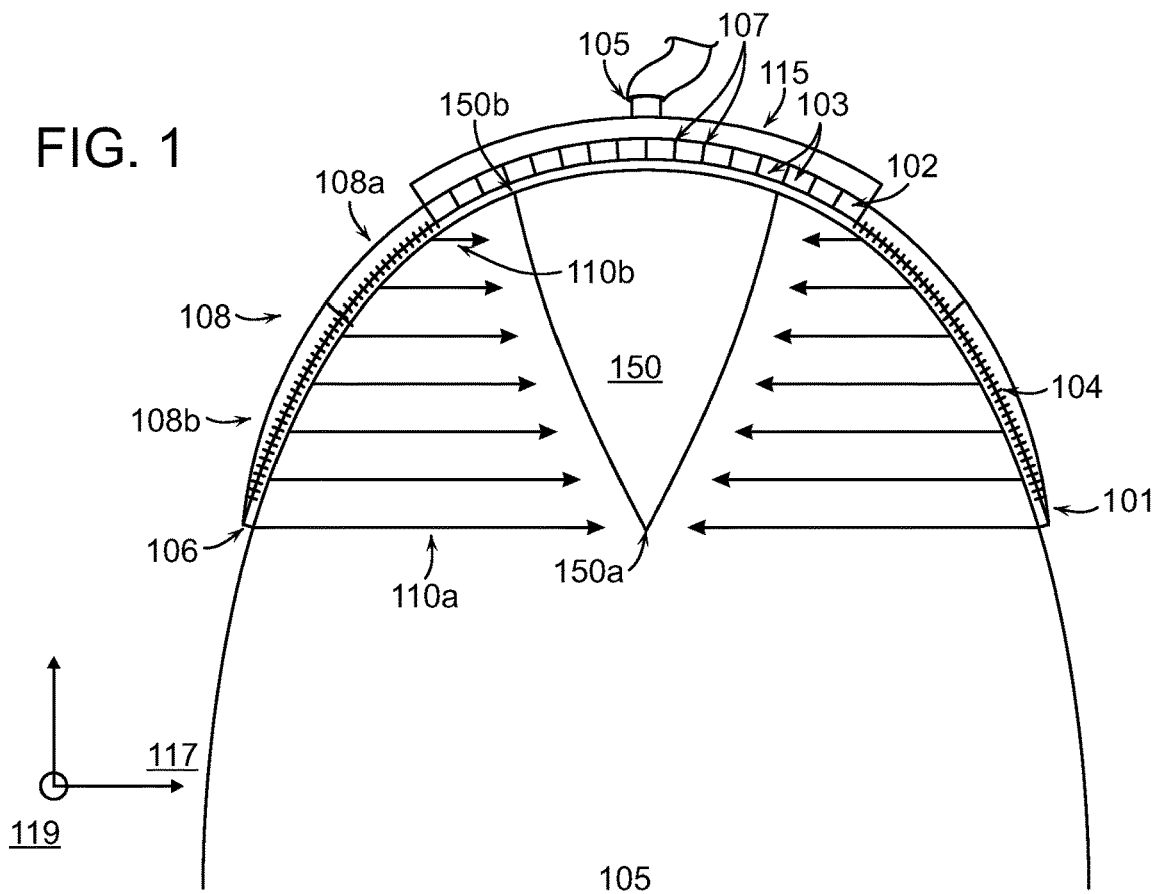
FIG. 1 illustrates a wound closure device applied to a wound in accordance with various embodiments of the present invention.

Embodiments of the present invention relate to negative pressure wound closure devices, systems, and methods for wounds resulting from amputation or other open wound in which the wound margins undergo rotation to align and close. The embodiments as described herein include a negative pressure source and a compression structure that is placed on the wound to provide directed preferential closure. The compression structure can include a number of cells separated by rigid or semi-rigid membranes that are hinged together at joints. The structure changes conformation during a procedure to facilitate closure of the wound.

FIGS. 1-4 illustrate cross-sections of a wound closure device 100 applied at a body extremity to a wound 150 caused by amputation. The wound closure device 100 can include a compression structure 102, an inlet 105, and flaps 108. The wound closure device 100 can have a dome-shaped geometry in order to extend around the limb in such a way that the peripheral edge 101 of the dome fully surrounds the wound. When a negative pressure is applied to the inlet 105, the compression structure 102 and flaps 108 can apply a force to the wound 150 that is strongest at the deepest point of the wound 150a. The compression structure 102 in combination with the application of negative pressure can exert a force to the wound 150 to facilitate closure of the wound 150 from the deepest internal point 150a as illustrated in FIGS. 1-4 and as described in further detail below. Application of the device can impart a force to spaced-apart wound margins that is operable to move the wound margins to a more closed position.

Although the wound closure device 100 is described as having a dome shape (i.e., a curvature along two axes), it is also contemplated that embodiments of the present invention can have curvature in only one dimension (i.e., a cylindrical geometry). As a non-limiting example, a wound closure device 100 in accordance with the present disclosure can cover a wound on a lateral surface of a bodily limb or extremity such as the thigh. The device can have a range of values of curvature to accommodate wounded extremities as varied as fingers or toes to legs or arms. In some embodiments, the radius of curvature of the device is different from the radius of curvature of the tissue under treatment such that, as a result, the device is at least partially spatially separated from the tissue surface.

The wound 150 can have a width (X) 152 and a depth (Y) 154. In some embodiments, the depth 154 of the wound 150 can be between 0.1 and 1 times the width 152 of the wound 150. Previously available treatments may incompletely treat wounds with such large aspect ratios of depth to width because they typically force the margins of the wound at a shallow portion 150b of the wound to approximate (i.e., come into contact) before the margins of the wound at a deep portion 150a of the wound. In the case where the shallow margins approximate first, the potential arises for seroma formation or infection of the wound below the surface. Embodiments of the present invention can ameliorate this problem by preferentially applying a greater lateral force 110a at the deep portion 150a of the wound 150 than at the shallow portion 150b of the wound as will be described in more detail below.

The compression structure 102 can be situated outside of the wound as shown in FIG. 1A and can have a number of cells 103 separated by rigid or semi-rigid membranes 107 that are hinged together at joints. The shape of the cells 103 can be selected based on the shape of the wound 150. Details on the cell shape and composition will be described in greater detail below with reference to FIG. 5. The compression structure 102 can be pre-stressed to exert a compression force on the wound 150 to more quickly bring the wound margins together. Certain elements or cells of the compression structure can have greater compliance to enable interdigitated collapse. In some embodiments, the compression structure 102 can include a circle or spiral format that lays flat in or above the wound to achieve a similar collapsing effect. In various embodiments, the compression structure 102 can be symmetrical or asymmetrical. As the compression structure collapses, the outermost surface of the compression structure 102 can have a larger radius than the innermost surface of the compression structure 102. Note that the walls of adjoining cells extend at different angle due to the arced shape of the device that is needed to extend over the wound. For amputation wounds, the device must have a dome-shaped structure to enclose the wound opening at one end of the limb. In some embodiments, the compression structure 102 is a collapsible structure. The collapsible structure can have a curved contour that extends over at least a portion of tissue adjacent to the wound or wound opening.

The flaps 108 can be attached to the compression structure 102 and can extend to the peripheral edge 101 of the wound closure device 100. In some embodiments, the flaps 108 may include a first section 108a and a second section 108b that are made of different materials or have different properties. In certain embodiments, the first section 108a may be more flexible, stretchable, or elastic than the second section 108b. In some embodiments, the first section 108a, the second section 108b, or both may include anchoring elements 104. The anchoring elements 104 can be used with the flaps 108 on some or all sides of the wound 150 to attach the structure to a wrap 106 that surrounds the limb just proximal to the wound opening. In some embodiments, the second section 108b of the flaps 108 can be made of a stiff material that will not substantially change conformation as the compression structure 102 moves. This stiffness in a section of the flaps 108 can increase the closure force applied to the wound 150.

The wound closure device 100 can be covered with a cover element that can be custom-designed to fit the shape of a particular patient. In some embodiments, the cover element can include a foam or other biocompatible substance. The cover element may include prostheses or can be specially designed to distribute force due to body weight or pressure to prevent adverse wound events such dehiscence.

In some embodiments, a pump or other vacuum source can be used to apply negative pressure to the wound closure device 100. The pump can attach to the inlet 105 of the wound closure device 100. Additional vacuum sources can also be connected through an array of spaced inlets 105 in order to spatially distribute the suction force so that the force exerted on the compression structure 102 can be controlled separately from a fluid suction force. The amount of applied negative pressure can be adjusted depending on the size and shape of the wound. Pressures above 125 mm to as much as 250 mm or more can be used to assist in wound closure. The pressure can be reduced over time as the wound heals and reduces in size and depth. The vacuum source or pump can be further connected in some embodiments with a surgical drain device as described in greater detail below with reference to FIGS. 6, 11 and 12.

In accordance with various embodiments, the inlet(s) 105 can be disposed on an attachment plate 115. The attachment plate 115 may or may not be rigid along certain directions and may be smooth on one or more surfaces. The attachment plate 115 can overlay the compression structure 102 and may also exhibit elastic or stretching properties. The material of the attachment plate 115 can be biocompatible film such as that provided in conjunction with the Renasys® system available from Smith & Nephew. A preferred embodiment can also be used with a gauge as also provided in the Renasys® system. The smooth attachment plate 115 enables the compression structure 102 to contract and expand freely without interference from the underlying tissue, and without damaging the underlying tissue. In a preferred embodiment, the attachment plate 115 includes micropores that allow the passage of fluid through the attachment plate 115 and into the inlet 105 for removal from the wound site. In some embodiments, the attachment plate 115 can contact a wound filling material as described in greater detail below with reference to FIG. 6. In some embodiments, a drain or vacuum tube can extend through the attachment plate and into the wound filling material and/or to the surgical drainage device as described in greater detail below with reference to FIGS. 11-12E.

In some embodiments, the micropores can have different sizes in different regions and/or can have different pore densities in different regions in order to direct different force levels of the vacuum source to different regions of the device 100. Similarly, the compression structure 102 can be engineered with different internal cell sizes and/or cell densities to direct the distribution of forces from the vacuum source to different areas of the device 100.

The wound closure device 100 can be used without any sutures in cases where the skin edges on opposite sides of the wound 150 are sufficiently aligned. Alignment of the skin can be facilitated by surgically trimming the wound margins in advance of closure. In other cases, sutures can be selectively utilized to better align the skin on opposite sides of the wound 150. In various embodiments, the device can be used to treat a range of extremities including legs, arms, fingers, toes, hands and feet. After a period of healing, the device 100 can be removed and optionally replaced with a smaller device.

As described briefly above, the peripheral edge 101 can be designed to impart a greater lateral force 110a than, for example, the lateral force at a point 110b within the wound closure device 100. This gradient of closure force as shown in FIG. 1 can ensure that the maximum depth 150a of the wound 150 experiences a greater force 110a than the shallow depths 150b of the wound 150 to sustain wound margin contact during the application of negative pressure. It is desirable to have the wound margins initiate contact and healing at the deepest portion 150a of the wound 150 and progress from the deepest portion 150a to the shallowest portion 150b such that the skin on opposite sides at the surface of the wound 150 are the final portions of the wound margins to achieve closure. In many cases, the ends of the wound 105 undergo much smaller translation then the center. To accommodate this, the compression structure 102 can be configured with larger cells in the center and smaller cells at the ends of the wound in some embodiments.

In some embodiments, a seal may be included on the flaps 108 or cover element to seal the wound closure device 100 and prevent air from entering or leaving the device while the pressure is changed inside, e.g., by application of negative pressure. The seal can include elastics or adhesives to press a portion of the device 100 such as the peripheral edge 101 against the skin of the patient to produce an airtight seal. In certain embodiments, the seal is included at the peripheral edge 101 of the wound closure device 100.

Figure 2:
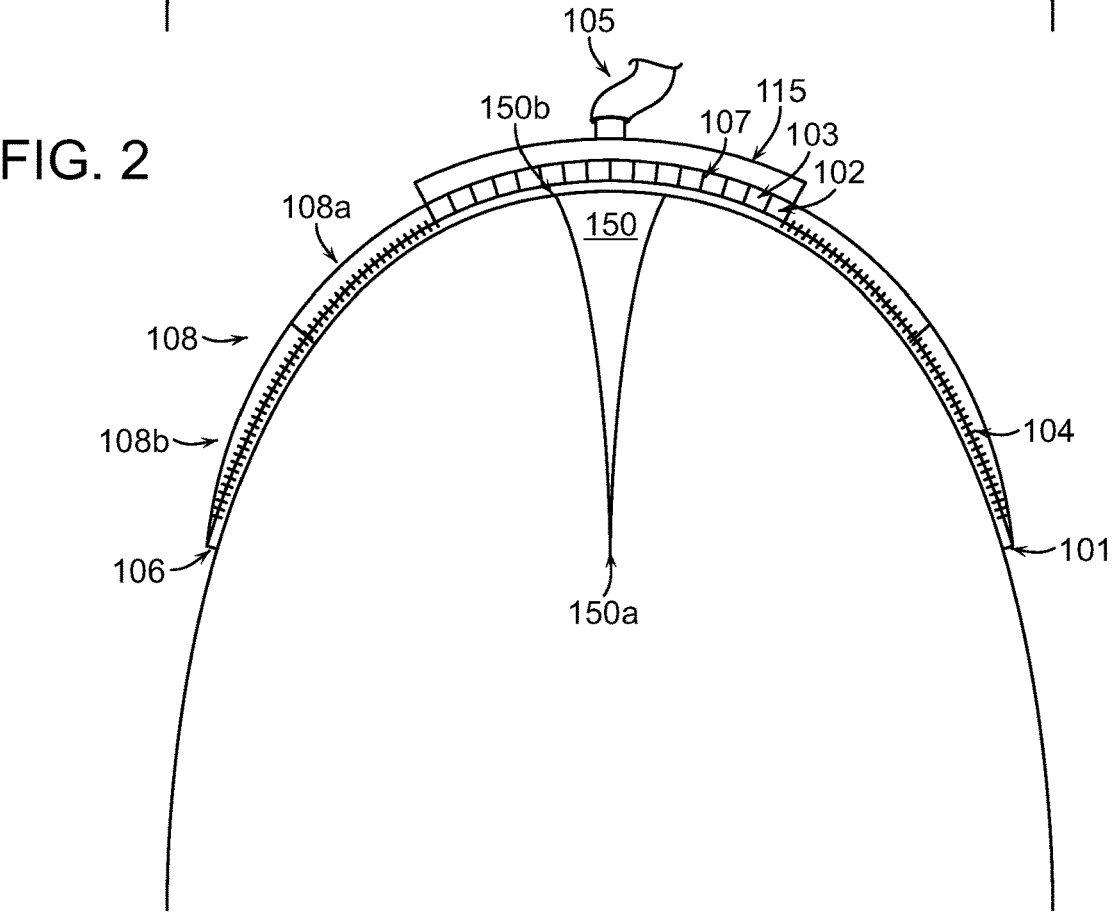
FIG. 2 illustrates a wound closure device applied to a wound after initial application of negative pressure in accordance with various embodiments of the present invention.
Figure 3:
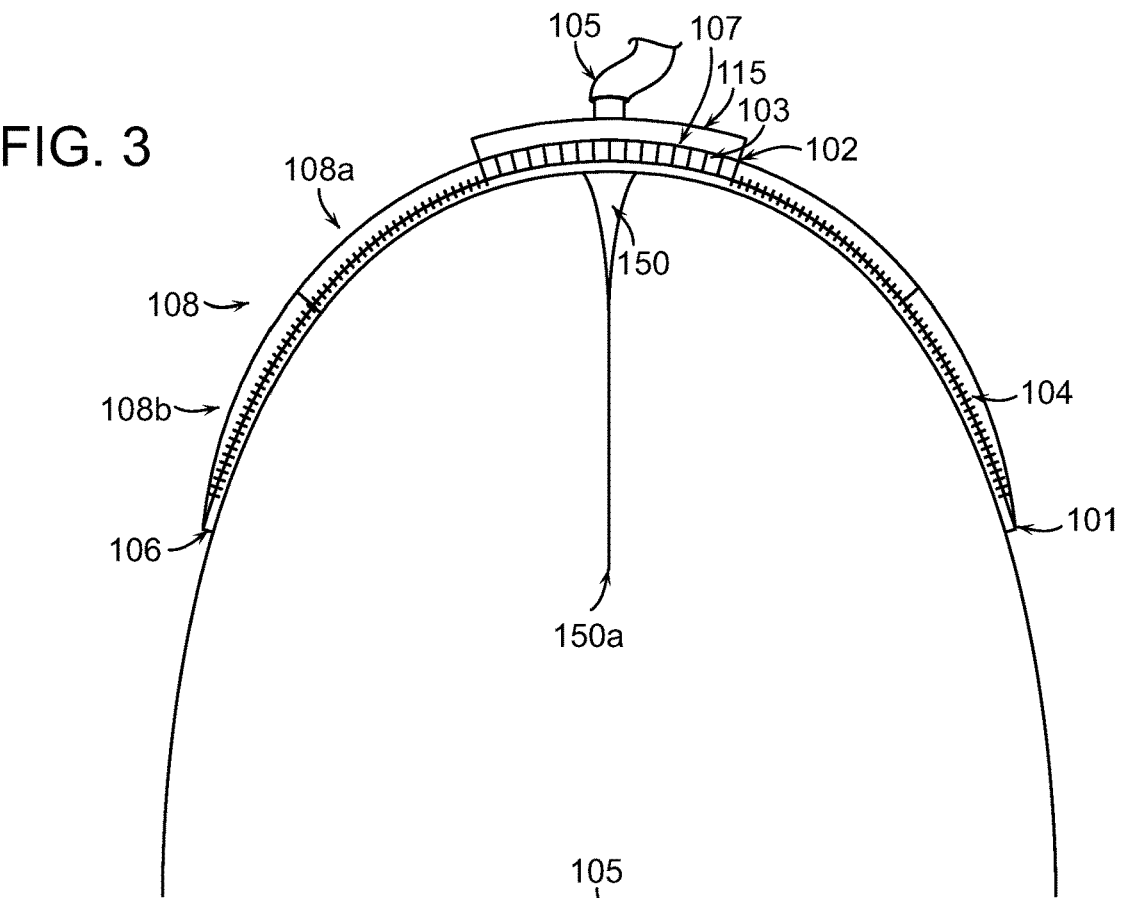
FIG. 3 illustrates a wound closure device applied to a wound after application of negative pressure in accordance with various embodiments of the present invention.
Figure 4:
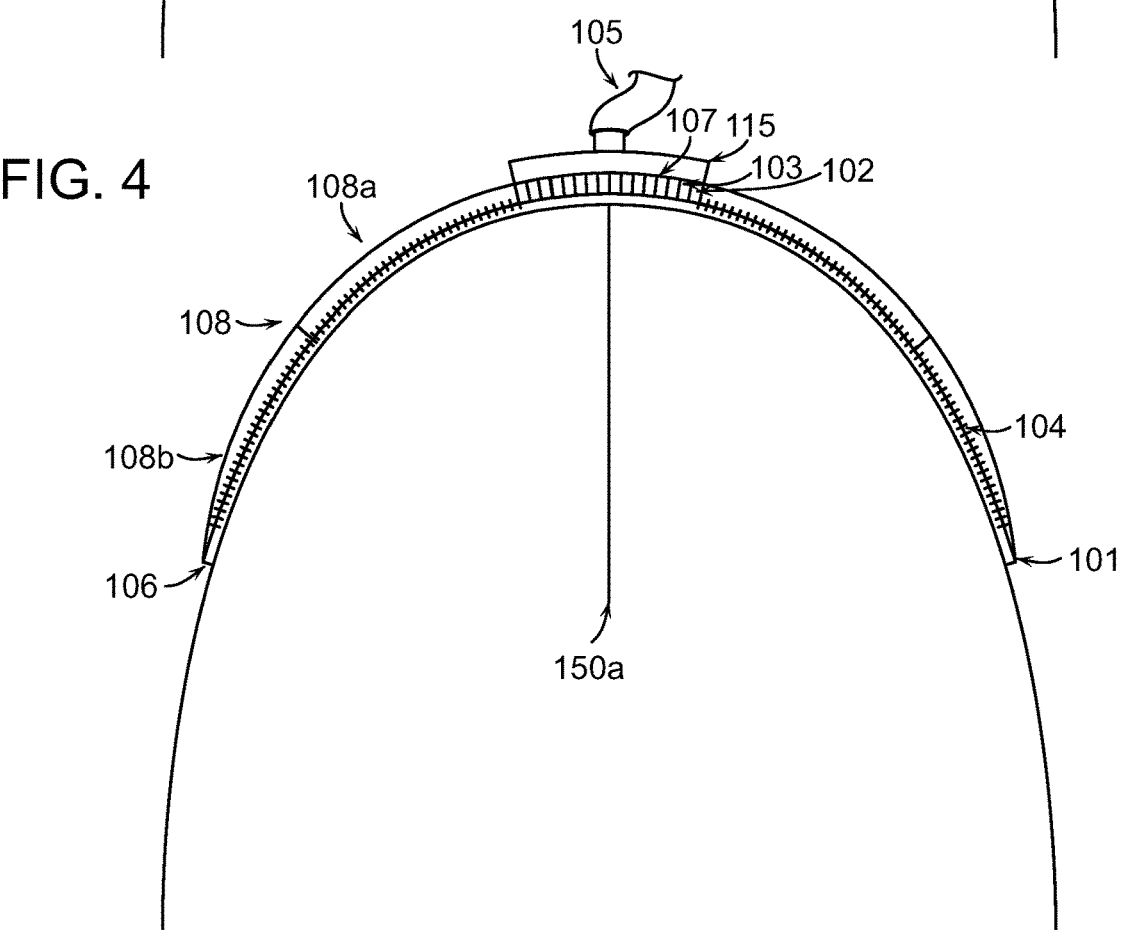
FIG. 4 illustrates a wound closure device applied to a wound after application of negative pressure in accordance with various embodiments of the present invention.

FIG. 2 shows the device of FIG. 1 shortly after negative pressure has been applied at the inlet 105. The negative pressure can cause the cells of the compression structure 102 to collapse in a preferred direction, e.g., length, width, or height. Due to the difference in forces 110a, 110b at different positions with respect to the wound 150, the wound margins on opposite sides at the deepest part 150a of the wound 150 move into proximity with one another. As the pressure continues to be applied (FIG. 3), the wound margins continue to come into contact from the deepest portion 150a to the shallowest portion 150b of the wound 150. Finally, after the negative pressure has been applied for some time, the wound margins on opposite sides are fully in contact (FIG. 4). The closure of the wound 150 from the deepest point 150a to the shallowest point 150b promotes healing and prevents the development of abscess or other pockets where bacteria can form. The wound closure device 100 can be left attached to the bodily extremity for an extended time period until wound healing is complete.

As shown in FIG. 5A, the compression structure 102 can have a three-dimensional geometry with cells 503 shaped as hexagons having internal membranes that can be arranged symmetrically or asymmetrically. In some embodiments, the cells 503 can include a plurality of polygonal shapes, irregular shapes, or both including, but not limited to, triangles, squares, parallelograms, pentagons, or any n-gon. In one embodiment, the cells 503 of the compression structure 102 can be a portion of a truncated icosahedron (i.e., a soccer ball). The cells 503 can be made of a pliable material.

In some embodiments, the interior of each cell 503 contains internal membranes or walls 505 to enhance structural stiffness in one or more directions. The internal membranes or walls 505 can be connected by hinged elements 506. As a result of this enhanced stiffness, the cells 503 can preferentially collapse along a specific dimension (e.g., length, width, or height) as shown in FIG. 5B. In accordance with various embodiments, a cell 503 can have a sufficient rigidity due to the presence of internal membranes 505 that the cell does not expand in a direction perpendicular to the preferred axis of compression or collapse. In some embodiments, this is accomplished through the use of single- or double-hinging. The internal membranes 505 of adjoining cells 503 can be oriented at different angles to accommodate the rotational component of the tissue movement during a wound closure procedure. These features can apply to any wound shape in which the wound margins undergo a more complex movement (compared to the substantially one-dimensional lateral movement of the abdominal walls associated with abdominal wound closure). Materials including structural elements, foam, tissue anchors, and operation of closure devices as described in International Patent Application PCT/US2013/050698, filed Jul. 16, 2013, and U.S. patent application Ser. No. 13/365,615, now U.S. Pat. No. 9,226,737, filed Feb. 3, 2012, and also U.S. application Ser. No. 13/942,493, now U.S. Pat. No. 9,421,132, filed on Jul. 15, 2013, the entire contents of the above-referenced applications and patents being incorporated herein by reference, can be used in conjunction with the devices and methods set forth herein.

FIG. 5C illustrates a three-dimensional view of a wound closure device 100 in accordance with embodiments of the present invention. The dome-shaped device can be broken up into cells 503 having one or more shapes as discussed above. In the embodiment of FIG. 5C, the cell shape is triangular and the triangles tessellate to form hexagonal structures. FIG. 5D illustrates a portion of a structure such as the dome-shaped device of FIG. 5C. In some embodiments, the device can include individual cells 503 that are substantially flat and are joined to one another through the use of hinges 508. The hinges 508 can allow relative movement and re-orientation of adjacent cells 503 to better conform the wound closure device 100 to a wound 150.

FIGS. 5E-5G are insets illustrating a portion of the wound closure device 100 indicated in FIG. 5A. In FIG. 5E, the walls between cells 503 are in their typical extended form. When negative pressure is applied in the device, the cells will contract in size as the wound margins begin to approximate as described above with reference to FIGS. 1-4. In some embodiments, the walls between cells 503 can include fold points at which the walls break or buckle to allow the cells 503 to contract in size as pressure is applied. The resulting walls upon folding are illustrated in top view in FIG. 5F and in perspective in FIG. 5G. In some embodiments, a network of cells 503 is rigid enough to compress and provide force to pull attached flaps 108. The flaps 108, in turn, can generate a force on attached tissue that surrounds the wound to provide a force to close the deep portion of the wound before the shallow portion.

Figure 6:
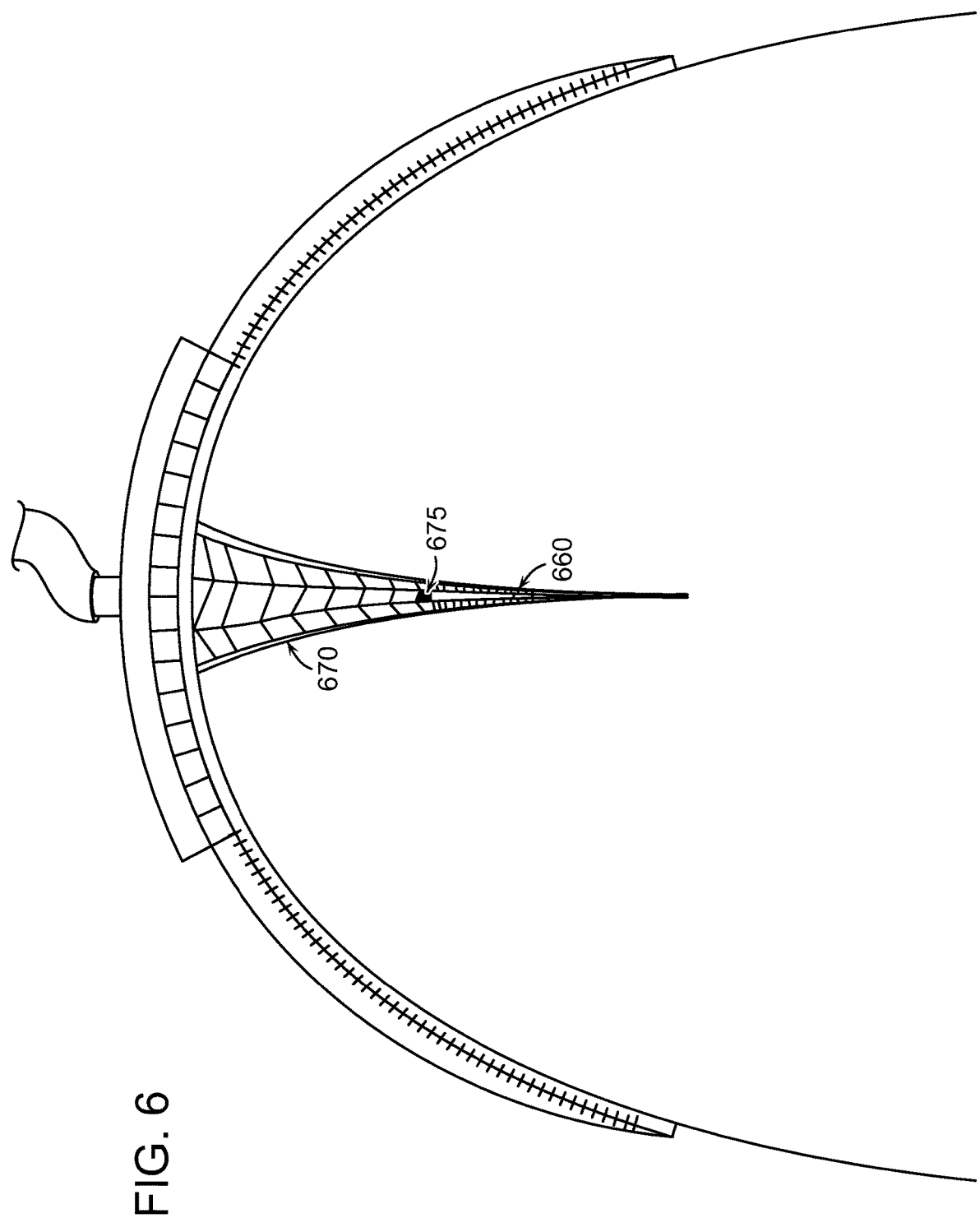
FIG. 6 illustrates a wound closure device including additional structural and drainage elements according to some embodiments of the invention.

FIG. 6 illustrates a wound treatment system 600 including a wound treatment device 100 that works in cooperation with additional structural and drainage features to accelerate wound healing in accordance with various embodiments of the present invention. The system 600 can include a surgical drain device 660 that attaches to the exposed wound surfaces in proximity to the deepest portion 150a of the wound 150. The surgical drain device 660 can include features and methods described in U.S. patent application Ser. No. 13/675,736, filed Nov. 13, 2012, International Application PCT/US2012/033608 filed on Apr. 13, 2012, now U.S. Pat. No. 10,166,148, and also in U.S. application Ser. No. 14/111,977 filed on Oct. 15, 2013, now U.S. Pat. No. 9,597,484, the entire contents of the above applications being incorporated herein by reference. The system 600 can also include a wound filler material 670 such as collapsing structure with foam elements and optionally including tissue anchors that attach to the wound margins that is placed in proximity to the shallow portion 150b of the wound 150.

The surgical drain device 660 can include apertures to allow wound margins on opposite sides of the drain device 660 to come into contact. In some embodiments, the surgical drain device 660 has a plurality of removable drainage tubes that can be withdrawn from the device. In various embodiments, the surgical drain device 660 is made of a bio-absorbable material such that the body of the device can be left in the wound 150 without needing to be removed. The material 670 can be attached to the tube elements 675 such that removal of material 670 from the wound 150 will extract the tubes 675 from drain device 660. The surgical drain device is described in greater detail below with reference to FIGS. 11-12E. In some embodiments, the tubes 675 can be similar to the plurality of drain tubes 30 as described below.

Figure 7A:
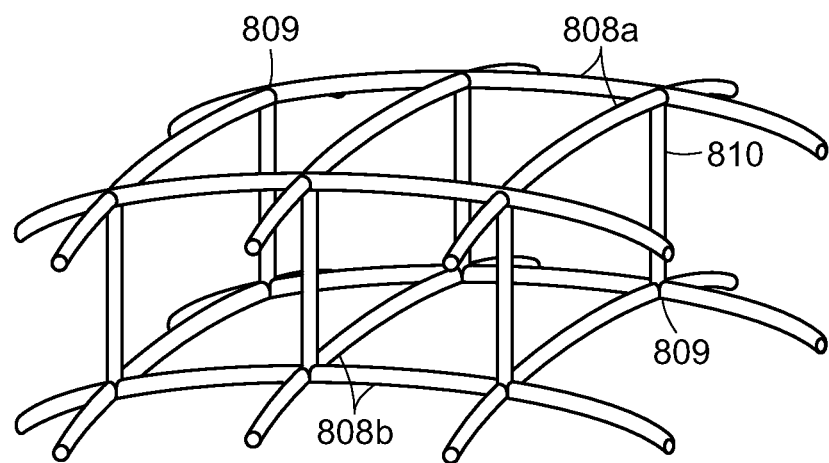
FIGS. 7A and 7B illustrate an exemplary cell structure for a compression structure in accordance with various embodiments of the invention.
Figure 7B:
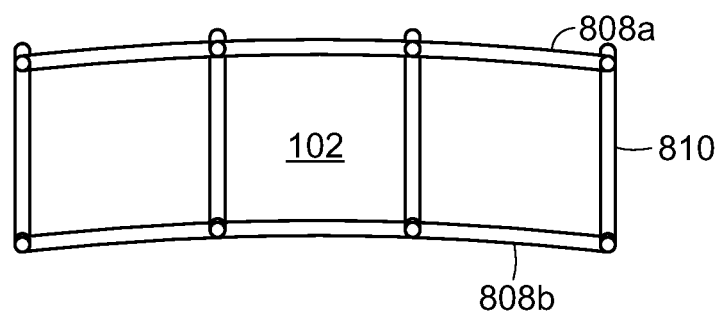

One embodiment of a cell framework for a compression structure 102 according to the invention is shown in FIGS. 7A and 7B. As discussed above, the compression structure 102 can have a curvature in one dimension (i.e., substantially cylindrical) or in two dimensions (i.e., substantially spherical or dome-like). The cells 502 can include a first set of x-y stabilizer elements 808a and a second set of x-y stabilizer elements 808b that are connected by a plurality of z-axis stabilizer elements 810. During collapse of the compression structure 102, the respective x-y stabilizer elements 808a, 808b are collapsible in the x-y directions, but the z-axis stabilizer elements 810 inhibit collapse in the z-direction. In preferred embodiments, the stabilizer elements can articulate with respect to one another during collapse. The joints 809 in the structure can be hinged or have a reduced thickness to accommodate the flexing of the system. Note that the first, upper set of stabilizer elements 808a is longer than the second, lower set of stabilizer elements 808b. The flexures between the joints may also flex to accommodate the desired compression along a first, or lateral, axis 117. Some expansion can occur along the second, or longitudinal, axis 119 as the device compresses. The material of the compression structure 102 can have a shape memory characteristic that, in combination with the force due to negative pressure, defines the force level applied to the tissue. In some embodiments, the stabilizer elements 108 can include a plurality of stabilizing ribs, flexures or rods, made from a suitably rigid or semi-rigid material, such as plastic. The spacing between the elements in the "open" state can be in a range of 1-2 cm, for example. In accordance with various embodiments, the first set of x-y stabilizer elements 808a disposed on the outermost surface of the compression structure 102 can have longer segment lengths than the second set of x-y stabilizer elements 808b disposed on the innermost surface of the compression structure 102. In different embodiments, the first set of x-y stabilizer elements 808a disposed on the outermost surface of the compression structure 102 can have a larger or equal radius of curvature than the second set of x-y stabilizer elements 808b disposed on the innermost surface of the compression structure 102.

Figure 8A:
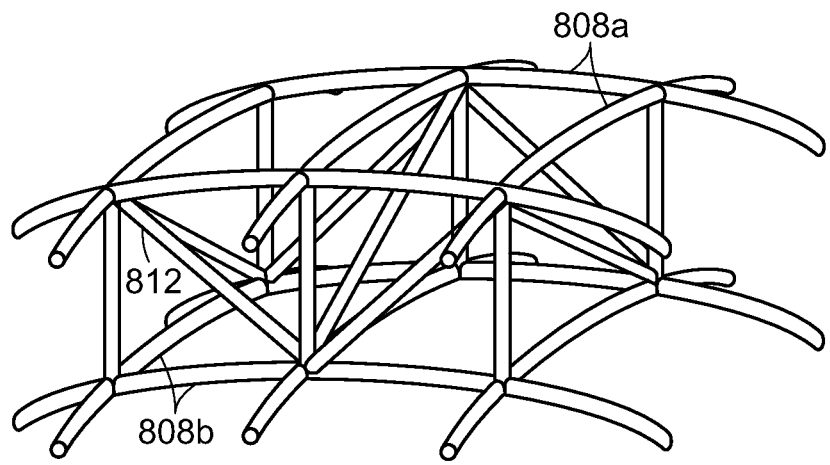
FIGS. 8A, 8B, and 8C illustrate further cell structure for a compression structure in accordance with various embodiments of the invention.
Figure 8B:
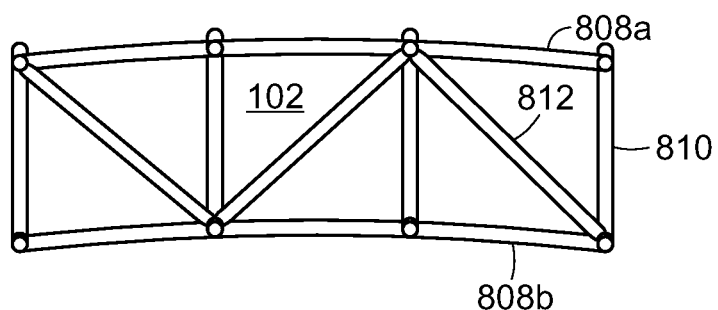
Figure 8C:
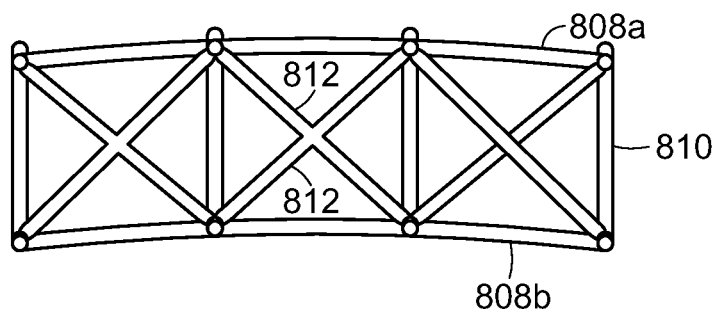

In another embodiment, shown in FIGS. 8A and 8B, the cells of the compression structure 102 can include truss stabilizers 812 to inhibit tilting of the structure 102 during collapse. The truss stabilizers 812 keep the upper 808a and lower 808b x-y stabilizers aligned with one another as the compression structure 102 collapses. In some embodiments, the truss stabilizers 812 can be rigid in certain directions and relatively less rigid in other directions (for example, the truss stabilizer can be bowed) to promote collapse in certain directions. FIG. 8C illustrates an alternative embodiment having truss stabilizers 812 in an "x"-shaped pattern.

The cells 502 in certain embodiments can be made, in whole or in part, from a shape memory material. Various shape memory materials can be used which return from a deformed state (temporary shape) to their original (permanent) shape. This change in shape can be induced by an external stimulus or trigger. In one embodiment, the original or "permanent" shape of the wound closure device is the "collapsed" configuration. When the wound closure device is initially applied at the wound, the device can be deformed in a temporary expanded state. The device can preferentially revert to its original or "collapsed" state or, alternatively, cause the device to first expand to engage the tissue. The "collapse" force of the shape memory structure can be in addition to or an alternative to the vacuum force induced by the negative pressure source. In certain embodiments, the application of a negative pressure to the wound closure device can cause the device to revert to its original state.

FIG. 9 illustrates an enlarged view of a preferred embodiment of a tissue anchor system 400 in accordance with some aspects of the invention. One side of the flaps 108 can have a first group of anchor elements 404 that are adapted to grasp the wrap 406 and/or the tissue. The first anchor elements 404 can be shaped to grasp the wrap 106 such as with a distal hooked shape 406. As the flaps 108 attach to the wrap 106 with a certain grasping strength in order to sufficiently affix the wound closure device to the bodily extremity, a specified force level F must be applied to remove the anchor elements 404 from the wrap 408 that exceeds the pulling force being applied to the device 100.

In some embodiments, the flaps 108 can attach at least in part to the tissue of a patient including dermal tissue. As the tissue to be grasped by the flaps 108 has different structural characteristics then the wrap 106, a second group of anchor elements can be adapted to grasp tissue and can have a different shape and grasping force then the first anchor elements 404. As discussed in greater detail below, barbs can have bilateral prongs that tend to collapse upon insertion in tissue and yet expand when pulled in an opposite direction such that a certain pulling force can be applied to tissue as the compression structure 102 collapses. However, the prongs or cone shape anchor element can have a release force such that the barbs can be manually pulled from the tissue without causing injury. In some embodiments, the flaps 108 attach to both tissue and the wrap 106.

The characteristics of the anchors, and their resulting force profiles, can vary by a number of parameters, such as the length of the anchor, the shape of the anchor, the structure of grasping features, the material(s) used for the anchor, the relative flexibility/rigidity of the anchors, and the spacing/density of the anchors. FIG. 10 illustrates three examples of different types of grasping features, including a barbed configuration 605, a staggered hook configuration 606, and a staggered barbed configuration 607. The anchoring process can be augmented by the application of a seal as described above. The force profile can also be varied by controlling the vacuum force distribution in the compression structure 102, such as by varying the cell size and/or cell density of the compression structure 102.

Figure 11:
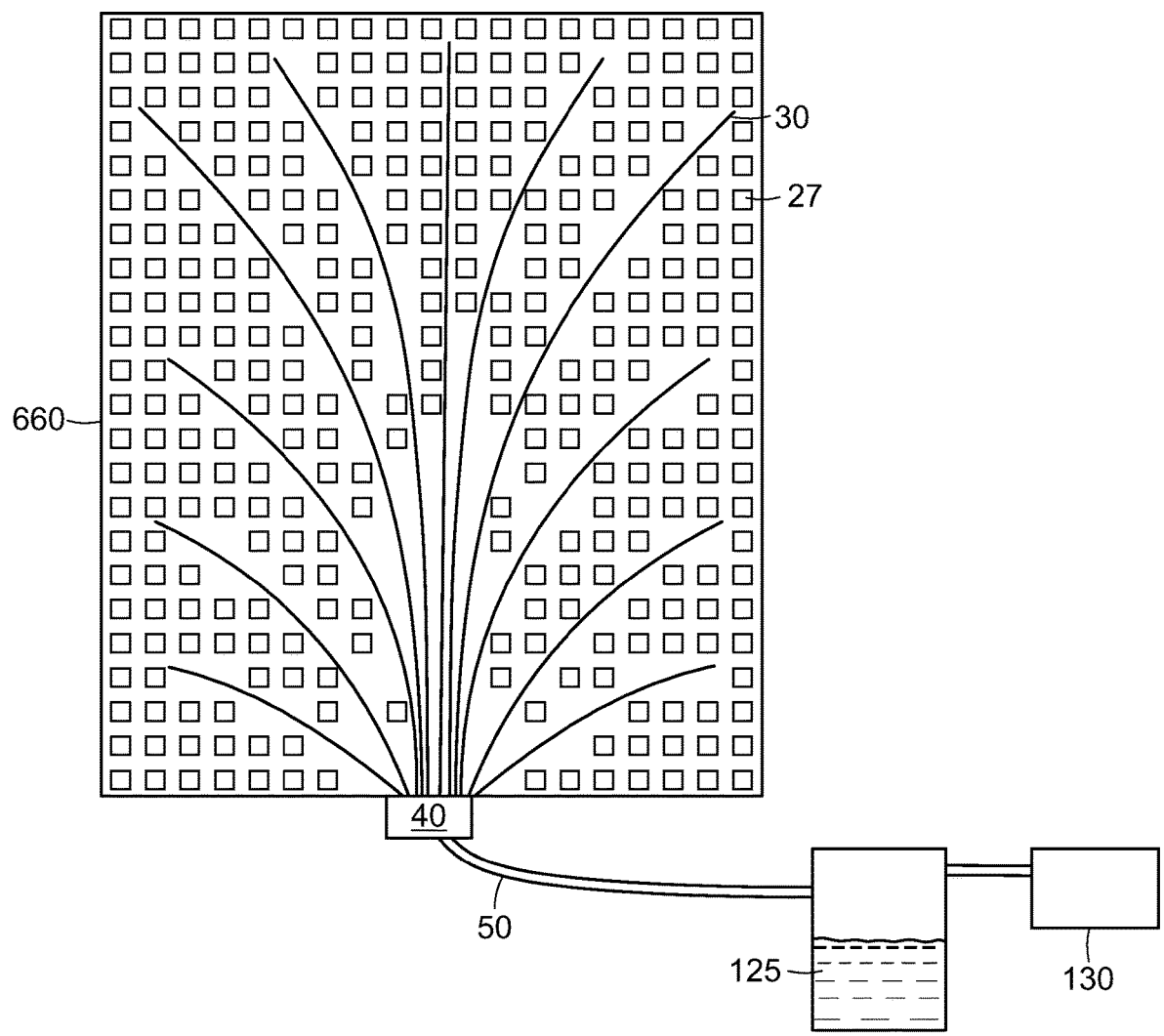
FIG. 11 is a schematic diagram of a surgical wound drainage device and related equipment according to some embodiments of the invention.

FIG. 11 schematically depicts a surgical drain device 660 and accompanying support equipment for drainage of at least a portion of a wound. The surgical drain device 660 can have a plurality of drain tubes 30 attached to an adhesion matrix 25 and configured so as to drain the full extent of the portion of the wound. The drain tubes 30 can be connected at their proximal ends to a manifold 40 that can in turn be connected through vacuum tubing 50 to a vacuum pump 130 or other vacuum source. Fluid 125 drained from the wound can be optionally accumulated in fluid trap 120. In some embodiments, the vacuum tube 50 and manifold 40 connect to a valve or port in the wound filler material 670. In this embodiment, removal of the wound filler material 670 (i.e., at the end of a wound closure operation) can release the manifold 40 and attached plurality of drain tubes 30 from the surgical drain device 660. The adhesion matrix 25 can be made of a bioabsorbable material and may be left in the body once the drain tubes 30 have been removed. Vacuum pump or other vacuum source 130 can include one or more electronic devices, such as a microprocessor with memory and software, to monitor the vacuum level, pneumatic resistance, and/or fluid removal amount or rate. The electronic device(s) also can be used to control the operation of the system over time according to user-defined parameters, according to a preset program, or in response to data collected on vacuum, resistance, and/or fluid removal.

The number of drain tubes in the surgical drain device 660 can vary depending upon the needs of the device, including the amount of fluid to be drained and the size of the wound and shape of the device. Typically, the device will contain from 2 to about 20 drain tubes. In a preferred embodiment, the device contains preferably at least 3 tubes, and for larger areas from about 5 to about 12 tubes.

The drain tubes 30 can be fabricated from any biocompatible thermoplastic or thermoset material. Examples include surgical grade silicone rubber, polyurethane, polyamide, polyimide, PEEK (polyether ether ketone), polycarbonate, PMMA (polymethylmethacrylate), and polyvinylchloride. The drain tubes 30 are intended to be removed after fluid build-up has reduced to a level that is stable without drainage. However, in an alternative embodiment, the drain tubes 30 can be made of a biodegradable material and can be left in place. The drain tubes 30 can be flexible so as to conform to the tissues surrounding the device and to accommodate movement of the patient without causing discomfort. The drain tubes can be open ended or close ended. In a preferred embodiment, the drain tubes are close ended and possess apertures or holes along their length for the uptake of fluid.

Figure 12A:
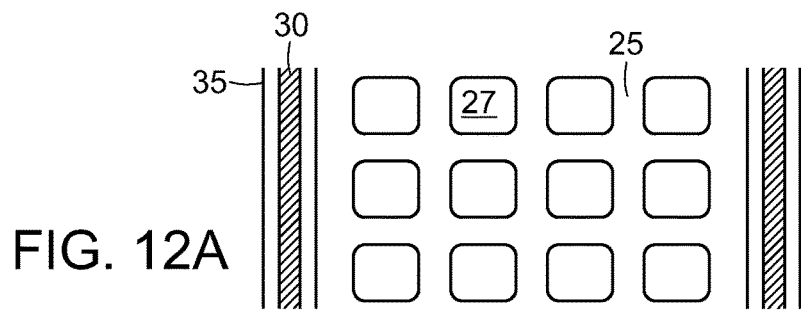
FIGS. 12A-C show illustrations of embodiments of an adhesion matrix having different types of tissue contact apertures.
Figure 12B:
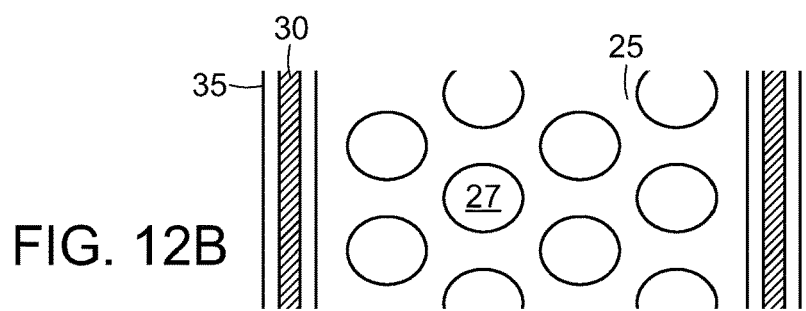
Figure 12C:
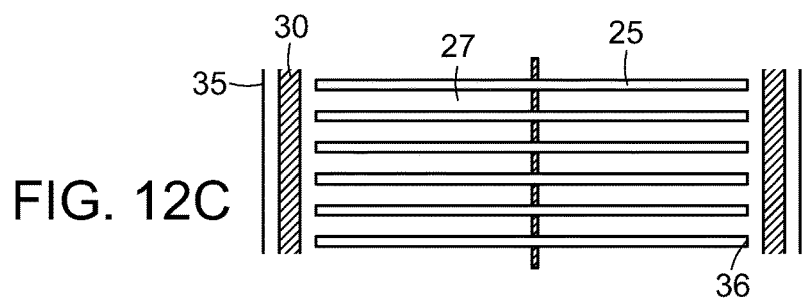
Figure 12D:
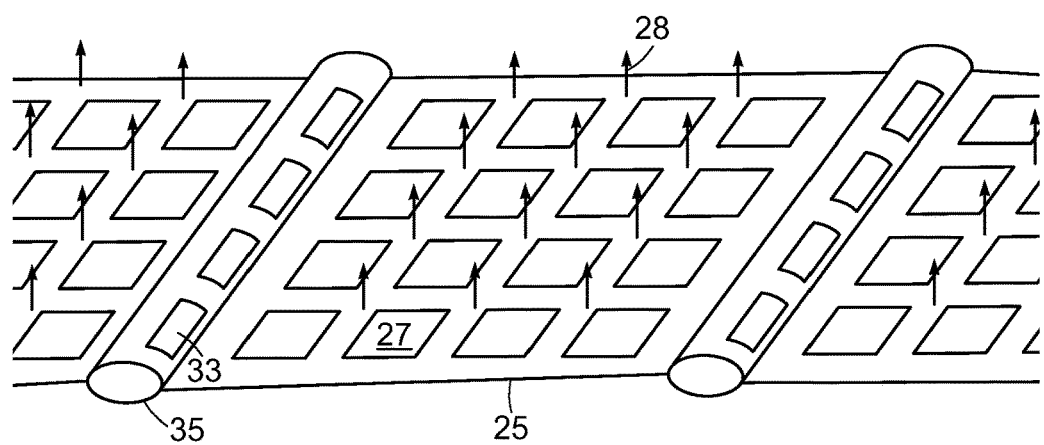
FIG. 12D is an illustration of an adhesion matrix embodiment possessing tissue anchors on its surface.
Figure 12E:
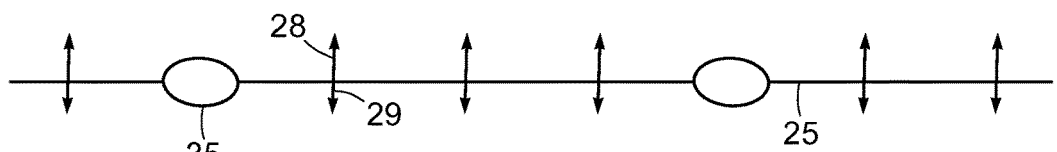
FIG. 12E shows a cross-sectional view of the adhesion matrix of FIG. 12D.

FIGS. 12A-E show several embodiments of the adhesion matrix 25. A portion of the adhesion matrix 25 between two neighboring drain tubes 30 and drain channels 35 is shown. The embodiment shown in FIG. 12A has a regular arrangement of rectangular apertures 27 to allow tissue contact through the device. This tissue contact enables a faster healing rate at the apertures 27. Circular apertures are shown in FIG. 12B. The embodiment of FIG. 12C includes apertures 27 that are formed into lateral channels. Fluid flows laterally through these channels toward openings 36 in the drain tube channels 35, drawn by the reduced pressure in the drain tubes 30. As shown in FIGS. 12D and 12E, the surfaces of the adhesion matrix, including the drain channels, can be endowed with an array of hooks or barbs to promote anchoring of the device to adjacent tissues. In the embodiment shown in FIG. 12E, the hooks on the upper side 28 are longer than the hooks on the lower side 29. This arrangement can be used where the tissues on either side of the device are of different density. For example, longer hooks such as about 1.5 to about 3 mm in length are preferred for less dense tissue, such as subcutaneous fat tissue, whereas shorter hooks such as about 0.5 to about 1.5 mm in length are preferred for denser tissues such as fascia and muscle.

The adhesion matrix 25, including any drain tube channels 35 and hooks or barbs, can be fabricated from a biodegradable polymer material, as these structures are intended to remain in place in the patient's body after removal of the drain tubes 30, so as not to disrupt the healing process. Examples of suitable biodegradable or resorbable materials include Vicryl (polyglycolic acid), Monocryl (glycolic acid-ε-caprolactone copolymer), PDS (polydioxanone, PDO), PLA (polylactic acid, polylactide), PLLA (poly-L-lactic acid), PDLA (poly-D-lactic acid), PGA (polyglycolic acid, polyglycolide), PLGA (poly(lactic-co-glycolic acid)), MB (polyhydroxybutyrate), and PCL (polycaprolactone). In a preferred embodiment, the adhesion matrix 25, including any drain tube channels 35, is formed of an open network of polymer chains that has sufficient porosity to allow infiltration by cells and fluid flow across the material. Cellular infiltration can promote tissue adhesion and the biodegradation of the polymer after the wound has healed. In some embodiments, the adhesion matrix 25 including any drain tube channels 35 is permeable to seroma fluid but not permeable to cells. In other embodiments, the adhesion matrix 25, including any drain tube channels 35, is permeable to fluid and electrolytes but is impermeable to proteins. The permeability properties of the matrix polymer material that makes up the basic substrate of the adhesion matrix 25 can be the same or different compared to the material that makes up the drain tube channels 35. In a preferred embodiment, the polymer chains, or fibers composed of polymer chains, of the adhesion matrix 25 are aligned along an axis substantially perpendicular to the axes of the nearest drain tubes 30. This alignment pattern promotes the flow of fluid through or along the surface of the adhesion matrix 25 towards the drain tubes.

The adhesion matrix 25, and thus the overall drain device 660, can have any form suitable for insertion into the wound or seroma where it is to be inserted. Generally, the form is that of a thin sheet or flexible planar mesh having an essentially rectangular shape. However, the shape can be rounded, circular, elliptical, oval, or irregular. Preferably the corners are rounded so as to minimize mechanical irritation of surrounding tissues. The size of the device is also determined by the particular use and anatomy of the patient. For example, the adhesion matrix can have an overall width and length in the range from about 2 cm to 25 cm, such as about 10 cm×12 cm or about 20 cm×25 cm. The thickness of the adhesion matrix 25 can be from about 0.5 mm to about 1 cm; where the sheet of material is preferably less than 5 mm in thickness and preferably the adhesion matrix 25 is about 1-2 mm thick. The thickness of the entire drain device 660, including the sheet of the adhesion matrix 25, drain tubes 30, and any hooks or glue pads is about 5 mm or less, 10 mm or less, or about 5-10 mm.

The adhesion matrix 25 can be coated with an adhesive material such as surgical glue either in addition to or instead of using hook or barb structures that stabilize tissue layers on either side of the drain device. Any type of surgical adhesive suitable for use within the body can be used, including polyethylene glycol polymers, adhesive proteins, gelatin-thrombin mixtures, albumin-glutaraldehyde, and fibrin-based sealants. Cyanoacrylates are to be avoided, as they cause inflammation if used internally. An adhesive coating can be placed on one or both surfaces of the adhesion matrix 25. Adhesive coatings can be applied to the device prior to its placement in a patient, i.e., as part of the device fabrication process. An adhesive coating can cover all or a portion of a surface of the device 660. A surgical adhesive can be used in the form of a fibrous mat or pad that is soaked or coated with an adhesive composition. The mat or pad is preferably fabricated from a biodegradable polymer, such as the type used to prepare the adhesion matrix 25. One or more layers of adhesive material can be placed between the device and surrounding tissue at the time of placement in the patient.

When the wound closure device 100 containing the compression structure 102 is applied to a wound 150 and negative pressure is applied, the wound margins will begin to approximate beginning with the deep portion of the wound 150a. As the wound margins rotate towards one another, the compression structure 102 must also compress along the lateral direction 117. Compression or collapse of the compression structure 102 can be achieved by several methods. FIGS. 13A-13F illustrate an embodiment of a portion of a compression structure 102 as it collapses in size. The compression structure 102 is depicted in an unstressed, expanded state in FIG. 13A (end view) and 13D (top cross-sectional view). In some embodiments, the expanded state may be the natural resting state of a compression structure 102. In the expanded state, the rigid or semi-rigid membranes 109 can be substantially perpendicular to the cell walls 107. In FIGS. 13B and 13E, the portion of the compression structure 102 is depicted in an intermediate state of collapse. In accordance with various embodiments, the membranes 109 can be joined to the walls 107 using hinges or any other attachment method that allows the membranes 109 to rotate or pivot with respect to the walls 107. The compression structure 102 is depicted in the collapsed state in FIGS. 13C and 13F. In some embodiments, the walls 107 of the compression structure 102 re-orient from a fan- or V-shape as seen in an end view to being substantially parallel in the compressed state. This rotation of the walls 107 mirrors the rotation of the wound margins as they begin to approximate during closure and healing of the wound 150.

Figure 13J:
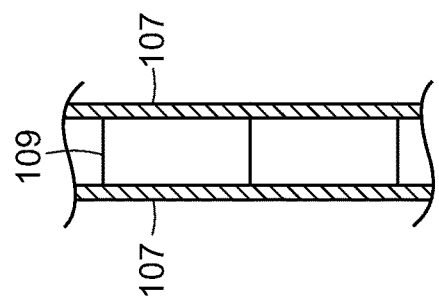
FIG. 13J illustrates a portion of a compression structure in a collapsed state in accordance with various embodiments of the present invention.
Figure 13H:
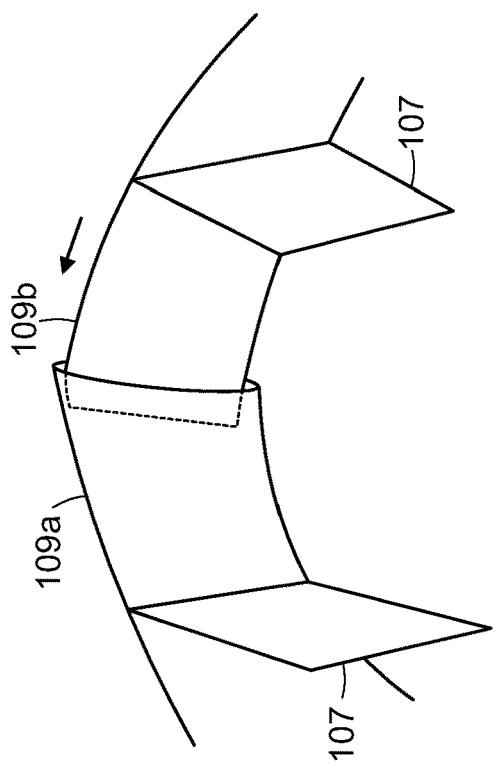
FIGS. 13H and 13I illustrate portions of the compression structure in extended and collapsed states, respectively, in accordance with various embodiments of the present invention.
Figure 13I:
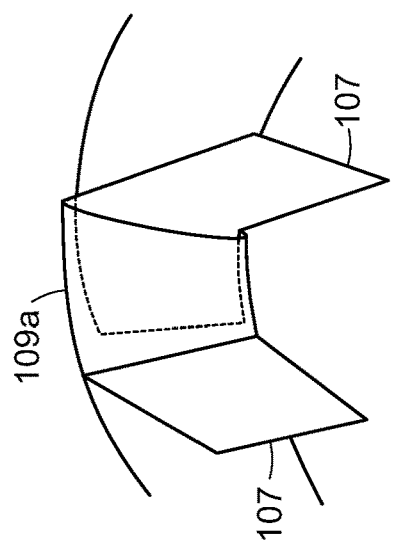
Figure 13G:
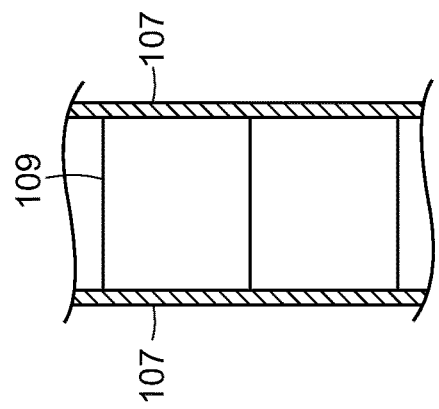
FIG. 13G illustrates a portion of a compression structure in an extended state in accordance with various embodiments of the present invention.

FIG. 13G illustrates a portion of a compression structure 102 including rigid or semi-rigid membranes 109 and walls 107 in accordance with various embodiments of the present invention. In accordance with various embodiments, the membranes 109 can include multiple interlocking sections such as an inner sliding section 109b and an outer sliding section 109a as shown in FIGS. 13H and 13I. In some embodiments, the inner sliding section 109b can be configured to fit partially or wholly within an adjacent outer sliding section 109a. In a first, extended state as shown in FIG. 13H, the inner sliding section 109b is withdrawn from the outer sliding section 109a to provide the maximum possible extension. As the compression structure 102 compresses, the inner sliding sections 109b will gradually slide into the body of the outer sliding sections 109a as shown in FIG. 13I. In some embodiments, the inner sliding section 109b can slide within an outer sliding section 109a until an adjoining wall 107 prevents further sliding. The resulting reduction in the total length of the membranes 109 is depicted in FIG. 13J.

Figure 14:
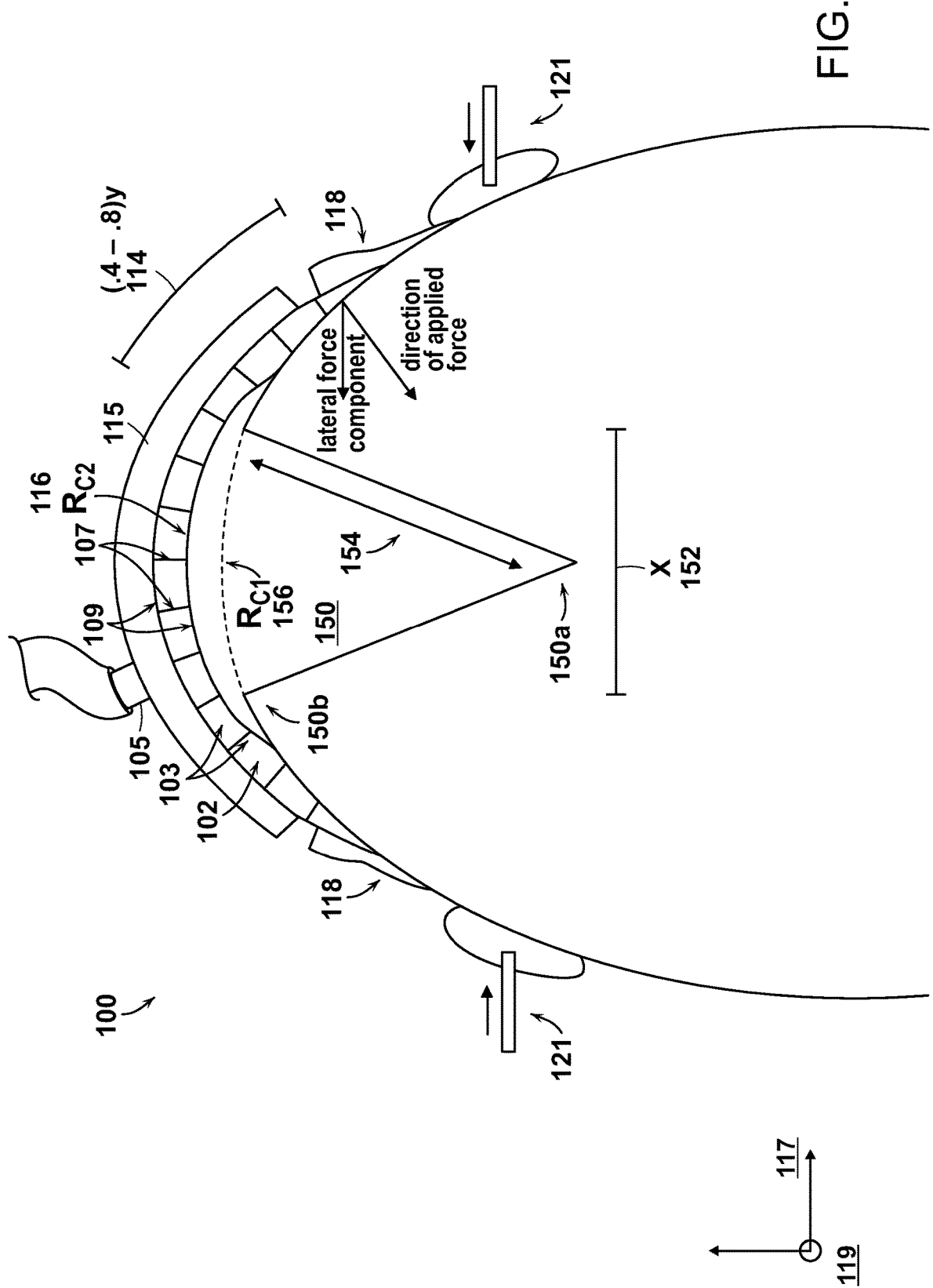
FIG. 14 illustrates a wound closure device with enhanced force application in accordance with various embodiments of the present invention.

FIG. 14 illustrates a cross-section of a wound closure device 100 applied at a body extremity to a wound 150 caused by amputation. The wound closure device 100 can include a collapsible structure 102, an inlet 105, and a drape 118. The wound closure device 100 can have a dome-shaped geometry in order to extend around the limb in such a way that the peripheral edge of the dome fully surrounds the wound. When a negative pressure is applied to the inlet 105, the collapsible structure 102 and drape 118 can apply a force to the wound 150 that is strongest at the deepest point of the wound 150a. The collapsible structure 102 in combination with the application of negative pressure can exert a force on the wound 150 to facilitate closure of the wound 150 beginning with the deep portion of the wound 150a.

Although the wound closure device 100 is described as having a dome shape (i.e., a curvature along two axes), it is also contemplated that embodiments of the present invention can have curvature in only one dimension (i.e., a cylindrical geometry). As a non-limiting example, a wound closure device 100 in accordance with the present disclosure can cover a wound on a lateral surface of a bodily limb or extremity such as the thigh. The device can have a range of values of curvature to accommodate wounded extremities as varied as fingers or toes to legs or arms. In some embodiments, the radius of curvature 116 of a portion of the device ($R_{C2}$) is different from the radius of curvature 156 of the tissue ($R_{C1}$) under treatment such that, as a result, the device is at least partially spatially separated from the tissue surface.

The wound 150 can have a width (X) 152 and a depth (Y) 154. In some embodiments, the depth 154 of the wound 150 can be between 0.1 and 1 times the width 152 of the wound 150. Previously available treatments may incompletely treat wounds with such large aspect ratios of depth to width because they typically force the margins of the wound at a shallow portion 150b of the wound to approximate (i.e., come into contact) before the margins of the wound at a deep portion 150a of the wound. In the case where the shallow margins approximate first, the potential arises for seroma formation or infection of the wound below the surface. Embodiments of the present invention can ameliorate this problem by preferentially applying a greater lateral force 110a at the deep portion 150a of the wound 150 than at the shallow portion 150b of the wound as will be described in more detail below. In accordance with various embodiments, a portion 114 of the wound closure device 100 can be positioned over tissue adjacent to the wound 150. In some embodiments, the length of the portion 114 adjacent to the wound 150 can be 0.4 to 0.8 times the depth 154 of the wound 150.

The collapsible structure 102 can be situated outside of the wound as shown in FIG. 1A and can have a number of cells 103 separated by rigid or semi-rigid membranes 107 that are hinged together at joints. The shape of the cells 103 can be selected based on the shape of the wound 150. Details on the cell shape and composition will be described in greater detail below with reference to FIG. 5. The collapsible structure 102 can be pre-stressed to exert a compression force on the wound 150 to more quickly bring the wound margins together. Certain elements or cells of the collapsible structure can have greater compliance to enable interdigitated collapse. In some embodiments, the collapsible structure 102 can include a circle or spiral format that lays flat in or above the wound to achieve a similar collapsing effect. In various embodiments, the collapsible structure 102 can be symmetrical or asymmetrical. As the collapsible structure collapses, the outermost surface of the collapsible structure 102 can have a larger radius than the innermost surface of the collapsible structure 102. Note that the walls of adjoining cells extend at different angles due to the arced shape of the device that is needed to extend over the wound. For amputation wounds, the device must have a dome-shaped structure to enclose the wound opening at one end of the limb. The collapsible structure can have a curved contour that extends over at least a portion of tissue adjacent to the wound or wound opening. As described above with reference to FIGS. 13A-J, the collapsible structure can include articulating elements that undergo rotational movement during closure of the wound margins within a wound such as an amputation wound. In some embodiments, the articulating elements can rotate at joints such that the collapsible structure collapses along a curved path above the wound opening.

The collapsible structure 102 can include rigid or semi-rigid membranes 109 connecting walls 107 between cells 103. The lower set of membranes 109 can form a surface having a smaller radius of curvature 116 than the radius of curvature 156 of the surface of the tissue proximate to the wound. In some embodiments, the smaller radius of curvature is enforced by stiffened or firm elements within the collapsible structure 102. The difference in the radius of curvature 116 of the collapsible structure 102 relative to the radius of curvature of the tissue surface can impart additional force at the lateral ends of the collapsible structure 102. In some embodiments, the firmness or stiffness of the radius of curvature of the collapsible structure 102 can help allow the structure to resist buckling when a negative pressure is applied at the port 105. In some embodiments, the collapsible structure 102 can include a lateral portion that can apply an inward force to the deep portion 150a of the wound 150 to cause the deep portion 150a to close before the shallow portion 150b. In accordance with various embodiments, the collapsible structure 102 can contact the portion of the tissue adjacent to the wound opening and can include a stiff edge.

The drape 118 can provide a leak-free seal between the wound closure device 100 and the tissue surface. In some embodiments, the drape 118 can be made from materials including plastics or tapes and further including biocompatible materials. In some embodiments, the drape 118 can include adhesives or surgical glues as described above with reference to the adhesion matrix 25. The drape 118 can improve sterility of the wound 150 during healing by preventing ingress of dirt or bacteria. In some embodiments, the drape 118 can affix a lateral portion of the collapsible structure 102 to tissue surrounding at least the deep portion 150a of the wound 150.

The wound closure device 100 can be covered with a cover element that can be custom-designed to fit the shape of a particular patient. In some embodiments, the cover element can include a foam or other biocompatible substance. The cover element may include prostheses or can be specially designed to distribute force due to body weight or pressure to prevent adverse wound events such dehiscence.

In some embodiments, a pump or other vacuum source can be used to apply negative pressure to the wound closure device 100. The pump can attach to the inlet 105 of the wound closure device 100. Additional vacuum sources can also be connected through an array of spaced inlets 105 in order to spatially distribute the suction force so that the force exerted on the collapsible structure 102 can be controlled separately from a fluid suction source. The amount of applied negative pressure can be adjusted depending on the size and shape of the wound. Pressures above 125 mm to as much as 250 mm or more can be used to assist in wound closure. The pressure can be reduced over time as the wound heals and reduces in size and depth. The vacuum source or pump can be further connected in some embodiments with a surgical drain device as described in greater detail above with reference to FIGS. 6, 11 and 12.

In accordance with various embodiments, the inlet(s) 105 can be disposed on an attachment plate 115. The attachment plate 115 may or may not be rigid along certain directions and may be smooth on one or more surfaces. The attachment plate 115 can overlay the collapsible structure 102 and may also exhibit elastic or stretching properties. The material of the attachment plate 115 can be biocompatible film such as that provided in conjunction with the Renasys® system available from Smith & Nephew. A preferred embodiment can also be used with a gauge as also provided in the Renasys® system. The smooth attachment plate 115 enables the collapsible structure 102 to contract and expand freely without interference from the underlying tissue, and without damaging the underlying tissue. In a preferred embodiment, the attachment plate 115 includes micropores that allow the passage of fluid through the attachment plate 115 and into the inlet 105 for removal from the wound site. In some embodiments, the attachment plate 115 can contact a wound filling material as described in greater detail above with reference to FIG. 6. In some embodiments, a drain or vacuum tube can extend through the attachment plate and into the wound filling material and/or to the surgical drainage device as described in greater detail above with reference to FIGS. 11-12E.

In some embodiments, the micropores can have different sizes in different regions and/or can have different pore densities in different regions in order to direct different force levels of the vacuum source to different regions of the device 100. Similarly, the collapsible structure 102 can be engineered with different internal cell sizes and/or cell densities to direct the distribution of forces from the vacuum source to different areas of the device 100.

The wound closure device 100 can be used without any sutures in cases where the skin edges on opposite sides of the wound 150 are sufficiently aligned. Alignment of the skin can be facilitated by surgically trimming the wound margins in advance of closure. In other cases, sutures can be selectively utilized to better align the skin on opposite sides of the wound 150. In various embodiments, the device can be used to treat a range of extremities including legs, arms, fingers, toes, hands and feet. After a period of healing, the device 100 can be removed and optionally replaced with a smaller device.

In many cases, the ends of the wound 105 undergo much smaller translation then the center. To accommodate this, the collapsible structure 102 can be configured with larger cells in the center and smaller cells at the ends of the wound in some embodiments.

The wound closure device 100 can also include a compression element 121 such as a clamp to increase the amount of force applied at the deep portion 150a of the wound. In some embodiments, the compression element 121 can include only discrete points of contact around the wound such as with a surgical clamp or distractor or can surround the wound at all sides such as with an elastic band. In some embodiments, the compression element 121 can include a tacky or rubberized surface or an adhesive to improve contact with the tissue and prevent relative movement of the compression element 121 over the tissue surface during wound closure.

Figure 15A:
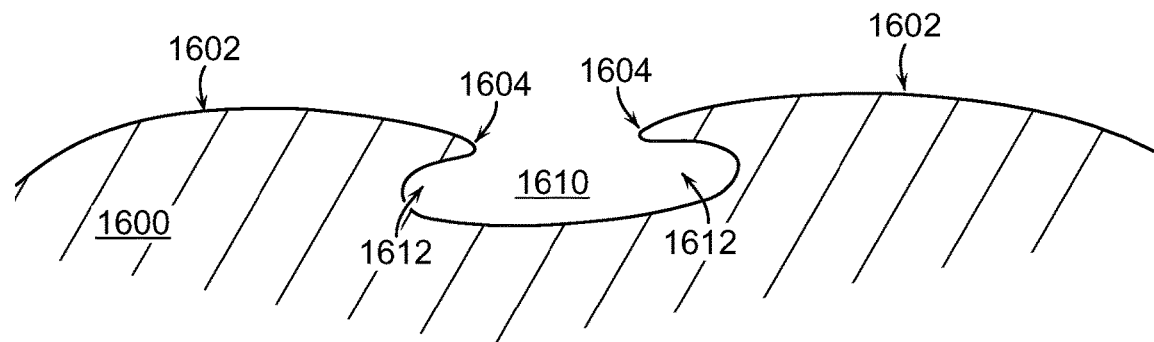
FIG. 15A illustrates a cross-sectional view of a decubitis ulcer injury in a tissue.

Some types of incisions and wounds are characterized by a greater area at the base (i.e., the deepest portion) of the wound than at the skin surface. FIG. 15A illustrates a cross-section of such a wound, which may be a pressure ulcer, a sacral decubitus ulcer, or an ischial decubitus ulcer in some embodiments. Such a wound could also be generated by drainage of a fluid-filled cavity such as an abscess or seroma. The inset wound 1610 is characterized by overhanging skin flaps 1604 that are undermined by a portion of the wound volume 1612. The undermined portion of the wound volume 1612 may create an especially difficult barrier to healing because of the risk of seroma or bacterial infection should the surface portion of the wound close before the margins in the hidden portion are properly closed. Due to the location and orientation of some ulcers of this type, the inset wound 1610 can lie in a concavity in the tissue 1600 with respect to high points 1602 surrounding the inset wound 1610. As a result, typical surgical dressings applied to the wound cannot apply sufficient pressure on the wound surface to effect proper drainage or to encourage the margins of the inset wound 1610 at the surface and in the undermined portion 1612 to properly approximate.

Figure 15B:
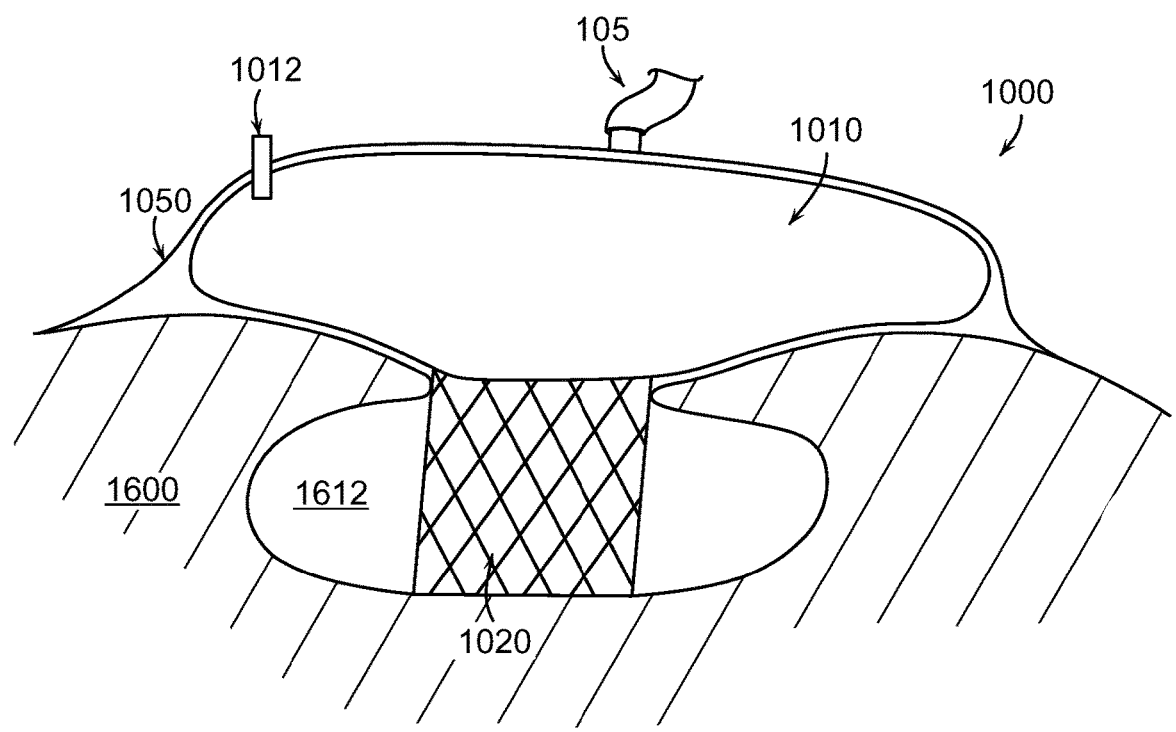
FIG. 15B illustrates a wound closure device applied to the decubitus ulcer injury according to various embodiments of the present invention.
Figure 15C:
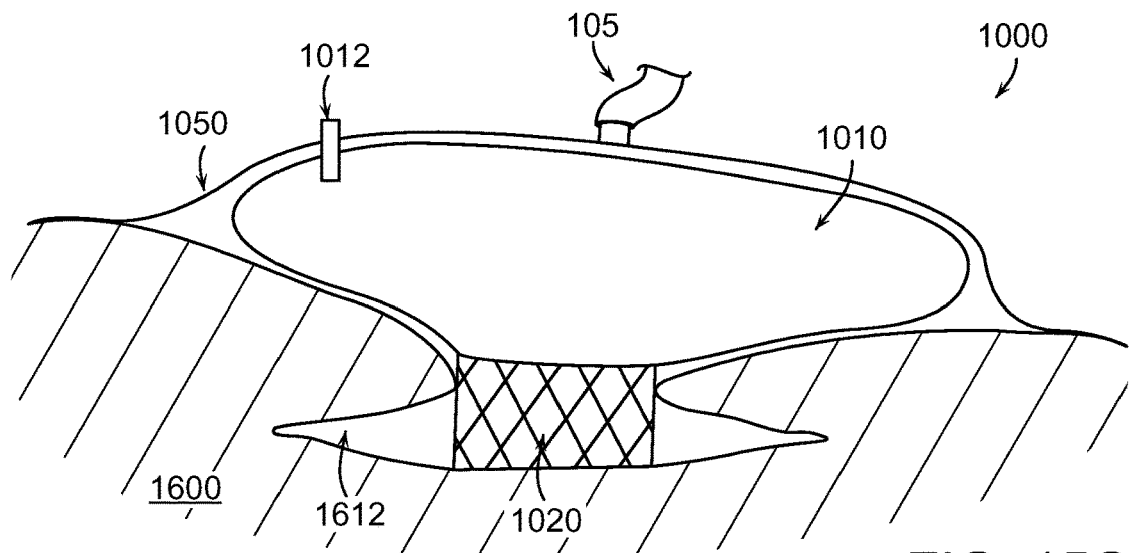
FIG. 15C illustrates the wound closure device of FIG. 15B upon application of negative pressure to the device in accordance with various embodiments of the present invention.
Figure 15D:
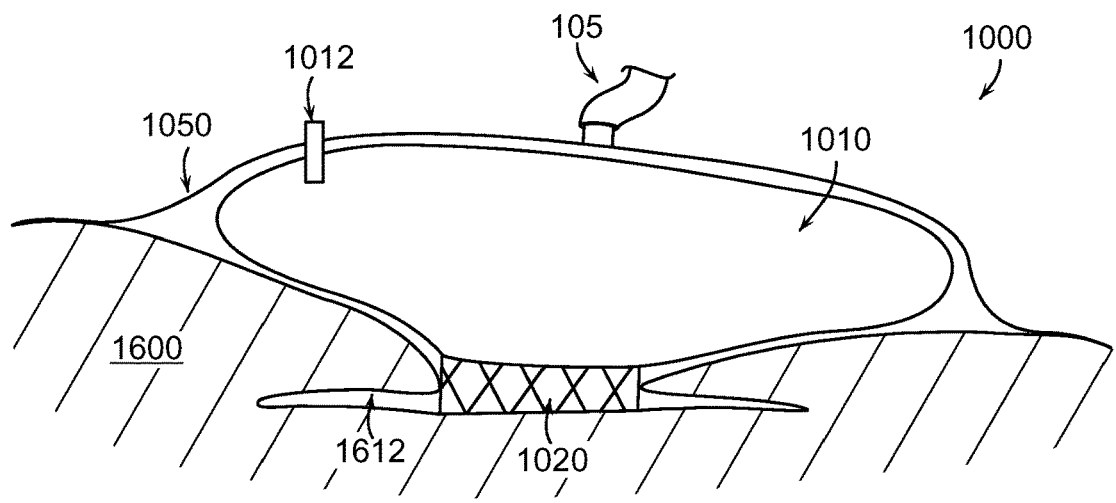
FIG. 15D illustrates the wound closure device of FIG. 15C wherein wound margins are nearly approximated in accordance with various embodiments of the present invention.

FIG. 15B illustrates a wound closure device 1000 that can be applied to an inset wound 1610 in accordance with various embodiments of the present invention. The wound closure device 1000 can include a compression element such as a bladder 1010, a drape 1050, an inlet 105, and a porous stem 1020. The wound closure device 1000 can be placed within the inset wound 1610. When negative pressure is applied at the inlet 105 as shown in FIG. 15C, the device 1000 can conform to the surface of the tissue 1600 and provide compressive force to the skin flaps 1604 to create apposition of the wound tissue under the skin flips and at the base of the wound. In some embodiments, additional compressive force can be generated by inflating or filling the compression element. By forcing the wound margins into apposition, the wound margins can approximate more quickly and can close off the undermined portion 1612 before approximation and closure occurs at the skin surface. An exemplary application of a wound closure device 1000 to bring the margins in the undermined portion into opposition is shown in FIG. 15D.

Figure 15E:
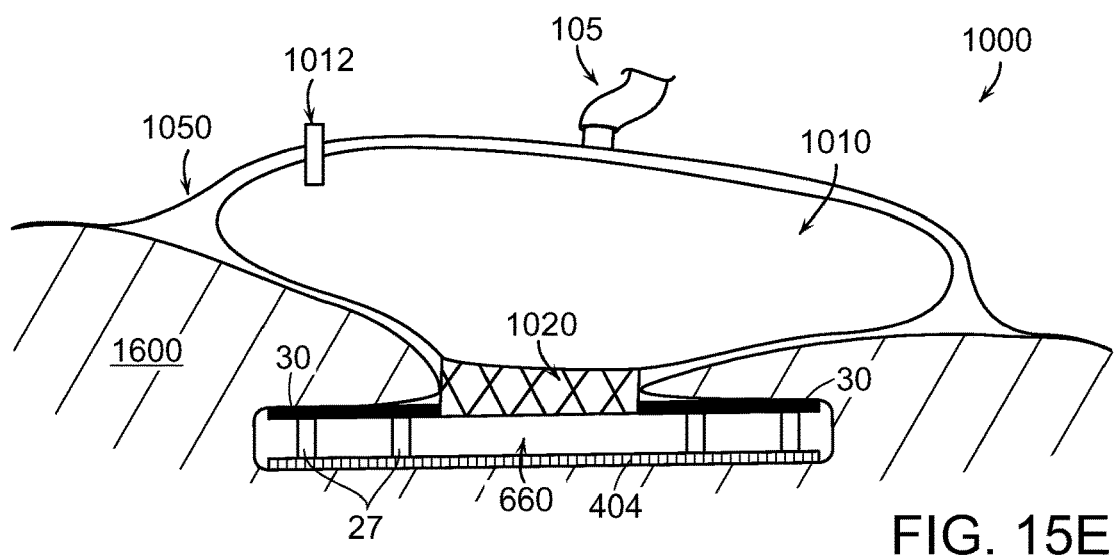
FIG. 15E illustrates a wound closure device that includes a surgical drain device in accordance with various embodiments of the present invention.

FIG. 15E illustrates a cross-sectional view of a wound closure device 1000 that includes a surgical drain device 660 in accordance with various embodiments of the present invention. The stem 1020 of the wound closure device 1000 can be in contact with at least a portion of the surgical drain device 660. As described above with reference to FIGS. 6 and 9-12E, the surgical drain device 660 can include apertures 27 to allow wound margins on opposite sides of the drain device to come into contact through the device. In some embodiments, the surgical drain device 660 can include drain tubes 30 to carry fluid from the wound 1610 to the stem 1020. In some embodiments, the drain tubes 30 can be attached to the stem 1020 or another element of the wound closure device 1000 and can be removed from the surgical drain device 660 when the wound closure device 1000 is removed from the wound 1610. In some embodiments, the surgical drain device 660 can include drain channels that are coupled to the stem 1020 to allow fluid to be drawn to the stem 1020 and out of the wound cavity.

In some embodiments, the surgical drain device 660 can include tissue anchors 440 as described previously. The tissue anchors 440 can attach to the wound margins on the underside of the skin flaps 1604 and at the base of the wound. In some embodiments, the tissue anchors 440 can improve approximation of wound margins that, due to tissue inelasticity or wound geometry, simply cannot stretch enough to meet under pressure from the bladder 1010.

In accordance with various embodiments, the stem 1020 can be a collapsible element that can collapse in both the horizontal and vertical directions (i.e., the depth and lateral directions according to the wound geometry). As negative pressure is applied, the stem 1020 can collapse in the vertical direction to allow wound margins in the undermined portion 1612 of the wound 1610 to approximate. The stem 1020 can also collapse in the horizontal direction to allow the wound margins in the surface portion of the wound (i.e., the skin flaps 1604) to approximate. In some embodiments, the stem 1020 can contain a collapsible structure as described above with reference to previous embodiments.

Figure 16A:
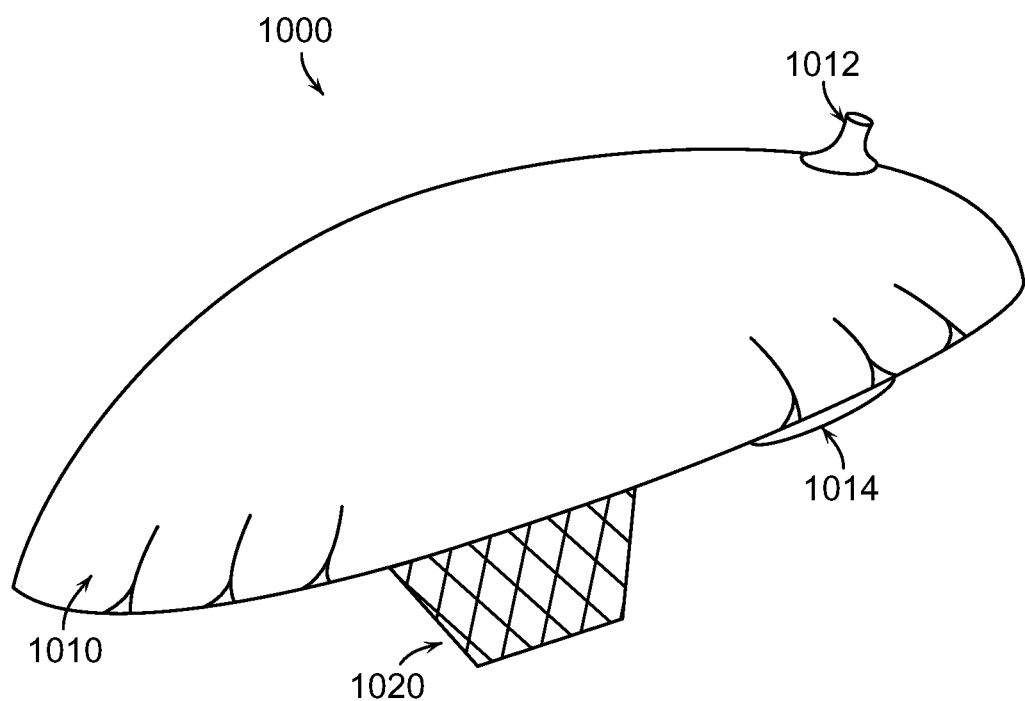
FIGS. 16A-16E illustrate wound closure devices to treat injuries characterized by undermining in accordance with various embodiments of the present invention.

FIG. 16A shows a perspective view of a wound closure device 1000 in accordance with various embodiments of the present invention. In accordance with various embodiments, the device 1000 can include a compression element such as a bladder 1010, a porous stem 1020, a port 1012, and a pressure sensor 1014.

The bladder 1010 of the wound closure device 1000 can be made of any suitable material including, but not limited to, plastics, rubbers, or fabrics. The bladder 1010 can have a level of malleability and compliance such that it can mold to fill irregularities across a tissue surface. In some embodiments, the bladder 1010 may be filled with air or other gases, liquids such as saline, or colloidal materials such as gels or foams. In some embodiments, the bladder can be inflated by introducing filler material through the port 1012. As a non-limiting example, the bladder 1010 can be filled by a pump such as a hand- or battery-operated portable pump. One skilled in the art will appreciate that other methods of filling the bladder 1010 are also contemplated as being within the scope of the present invention including in-house and other stationary pressure sources, mouth-blowing, and integrated pumps or micro-pumps mounted within or on the bladder 1010. In some embodiments, the pressure within the bladder 1010 can be adjusted by the patient. In some embodiments, the bladder 1010 can include an integrated or detachable pressure gauge to measure the level of pressure within the bladder 1010.

The porous stem 1020 can be made of any suitable material including, but not limited to, biocompatible foam or gauze. In accordance with various embodiments, the porous stem 1020 can compress as negative pressure is applied as shown in the transformation of the stem between FIGS. 15B and 15C. The porosity of the stem 1020 can allow fluids to be drawn up within or through the stem 1020 to facilitate drainage of the wound 1610.

As with most wounds, an inset wound 1610 may be sensitive to the applied pressure. If the applied pressure is too great, adverse healing may ensue due to restricted blood flow or other causes. The pressure sensor 1014 can detect the magnitude of the applied force on the tissue at the surface of the skin. In some embodiments, the pressure sensor 1014 may be connected to the inlet 1012 to relieve overpressure within the bladder 1010 when the level of pressure on the tissue surface is too high.

When applied to a wound 1610, the wound closure device 1000 can include a drape 1050 to create a leak-free seal between the wound closure device 1000 and the surface of the tissue 1600. In some embodiments, the drape 1050 can be made from materials including plastics or tapes and further including biocompatible materials. In some embodiments, the drape 1050 can include adhesives or surgical glues as described above. The drape 1050 can improve sterility of the wound 1610 during healing by preventing ingress of dirt or bacteria. In some embodiments, the drape 1610 can extend from the wound 1610 to beyond at least the high points 1602 of the surrounding tissue surface. In some embodiments, the drape 1050 includes an inlet 105 through which negative pressure may be applied to the wound closure device 1000.

Figure 16B:
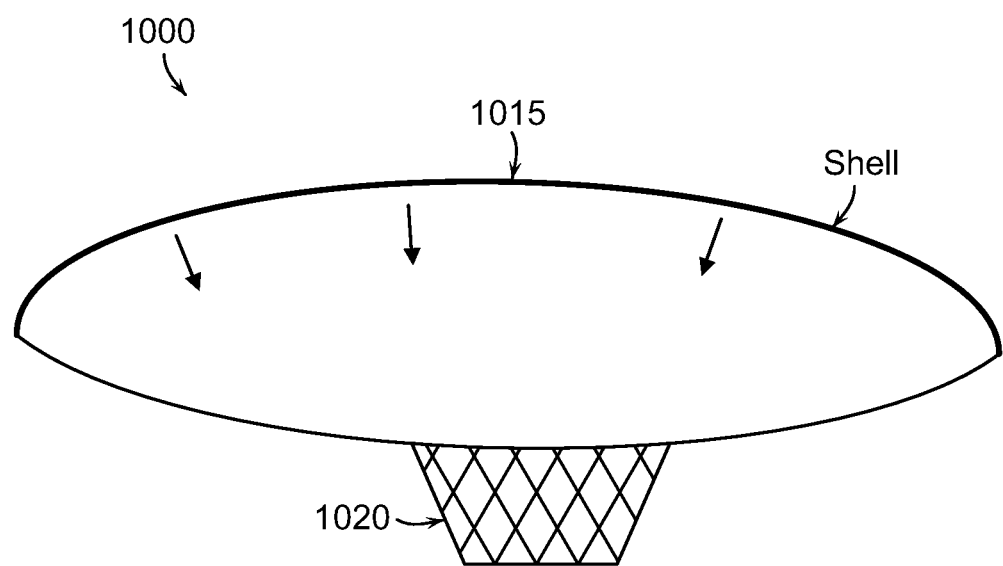

FIG. 16B illustrates a cross-sectional view of a wound closure device 1000 having a shell 1015 in accordance with various embodiments of the present disclosure. In various embodiments, the shell 1015 can be a separate external element attached to the bladder 1010 or can be integrated within the bladder 1010. The shell 1015 can be made of unyielding, firm, or rigid materials such that it holds its shape and is not pliable like the remainder of the bladder 1010. When negative pressure is applied to the device 1000, the drape 1050 will pull taut against the shell and apply pressure downward. Because of the rigidity of the shell 1015, the applied pressure will be primarily directed into the tissue 1600 (rather than into reshaping the bladder 1010) and thereby increase the overall force that can be applied to the skin flaps 1604 for the same level of negative pressure as compared to a device 1000 having no shell 1015.

Figure 16C:
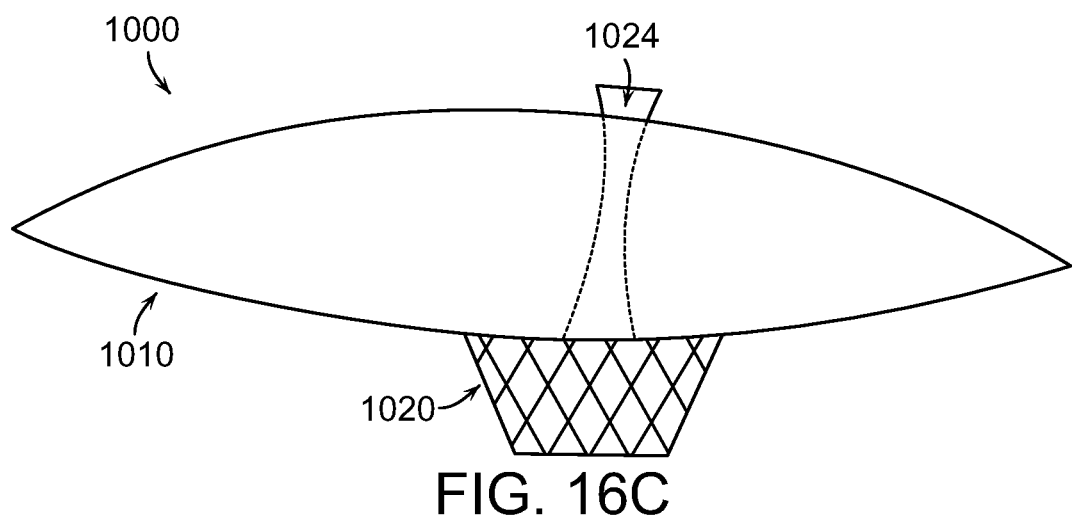
Figure 16D:
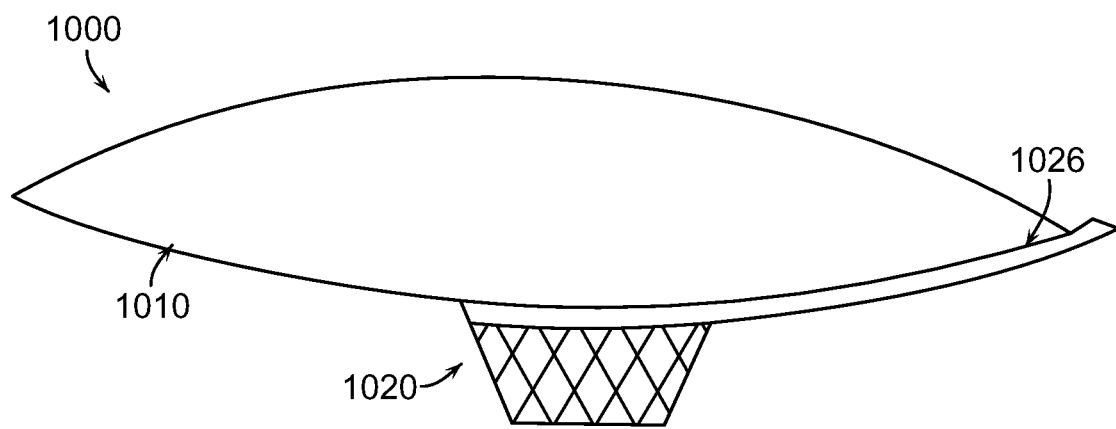

FIG. 16C illustrates a cross-sectional view of a wound closure device 1000 with a drain tube 1024 that passes through the bladder 1010. An alternative location of a drain tube 1026 is shown in FIG. 16D. In this embodiment, the drain tube 1026 passes below the bladder 1010 and beyond the bladder's periphery. In some embodiments, a pump can be connected to the drain tube 1024, 1026 to extract accumulated fluids via the porous stem 1020. In some embodiments, the drain tubes 1024, 1026 can be connected with the inlet 1012 to allow a single source of negative pressure to extract accumulated fluids and to create negative pressure within the wound closure device 1000.

Figure 16E:
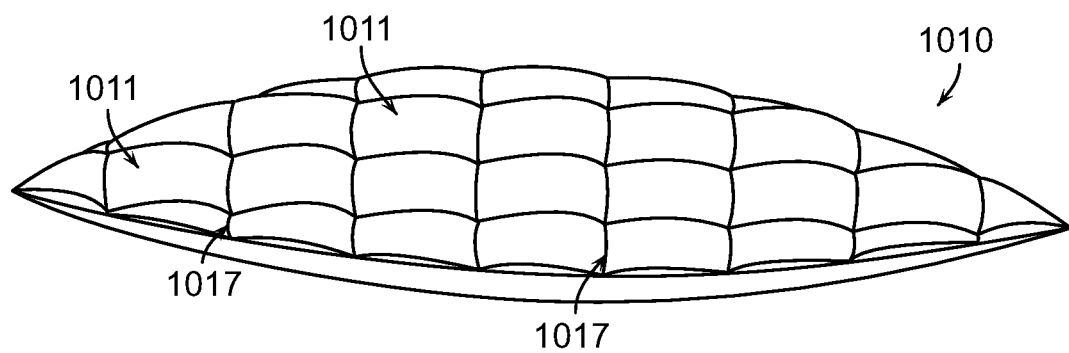

FIG. 16E illustrates an embodiment of a modular bladder 1010 in accordance with various embodiments of the present invention. The modular bladder 1010 may be made of individual sections 1011 separated by seams 1017. In some embodiments, the modular bladder 1010 may be cut or torn along the seams to remove sections 1011 until the desired bladder size is achieved. In accordance with various embodiments, each bladder section 1011 may be individually inflatable or fillable to provide different levels of pressure at different points on the bladder 1010. Although the modular bladder 1010 is depicted as having a grid of square sections, it is also contemplated that the modular bladder could include concentric ring sections, tessellating sections having other shapes than rectangles, or any other suitable shape as dictated by application-specific needs. In some embodiments, the seams 1017 can be self-sealing or self-healing such that each section 1011 becomes or remains pressurized or filled upon cutting or tearing at the seams 1017.

FIG. 17 illustrates an exemplary methodology 1200 for wound healing and closure in accordance with various embodiments of the present invention. In step 1202, an open wound at a body region having a depth including a deep portion and a shallow portion is surgically prepared for negative pressure wound therapy. For example, the open wound can be an amputation wound in a body region such as an amputated limb. A wound closure device is configured that includes a collapsible compression structure for the wound opening (step 1204). The configured wound closure device has a size and shape that conforms to the wound opening. The wound closure device is placed over the open wound (step 1206). Negative pressure is applied at a port or inlet to cause the compression structure to at least partly collapse (step 1208). The collapse of the compression structure causes the deep portion of the wound margins to close before the shallow portion. The wound closure device can optionally be removed and a second wound closure device can be applied to the wound (step 1210). The wound closure device can be removed, and the wound closure can be completed with or without sutures (step 1212).

FIG. 18 illustrates an exemplary methodology 1400 for wound healing and closure in accordance with various embodiments of the present invention. A wound in a tissue that has a depth including a deep portion and a shallow portion is surgically prepared for negative pressure wound closure therapy (step 1402). A wound closure device including a collapsible structure, flaps, and a port or inlet is configured (step 1404). The collapsible structure has a radius of curvature. Optionally, a surgical drain device is placed into the wound. The wound closure device is placed over the wound in the tissue (step 1406). A surface of the tissue surrounding the sound defines a radius of curvature that is greater than the radius of curvature of the collapsible structure. The tissue is optionally compressed on opposite sides of the wound while the wound closure device is attached to tissue surfaces surrounding the wound (step 1408). Negative pressure is applied at the inlet to cause the collapsible structure to at least partly collapse (step 1410). The collapse of the collapsible structure causes the deep portion of the wound to close before the shallow portion. The wound is drained of fluids during movement of the wound margins (step 1412). The wound closure device is removed from the wound, and the wound is closed with or without sutures (step 1414).

FIG. 19 illustrates an exemplary methodology 1500 for wound healing and closure in accordance with various embodiments of the present invention. A wound that includes an undermined portion and a surface portion is surgically prepared for negative pressure wound therapy (step 1502). A wound closure device is configured including a compression device, a drainage element, and a port or inlet (step 1504). For example, the compression device can be a bladder 1010 as described previously herein. The wound closure device is placed into the wound (step 1506). Negative pressure is applied at the inlet to cause the bladder to exert pressure on a surface of the tissue (step 1508). The pressure exerted by the bladder causes the undermined portion of the wound to close before the surface portion. The wound is drained of fluids through the drainage element during movement of the wound margins (step 1510). The wound closure device is removed from the wound, and the wound is closed with or without sutures (step 1512).

FIG. 20 illustrates an exemplary methodology 1700 for wound healing and closure in accordance with various embodiments of the present invention. A wound in a tissue that includes an undermined portion and a surface portion is surgically prepared for negative pressure wound therapy (step 1702). A wound closure device including a compression device, a drainage element, and a port or inlet is configured (step 1704). The drainage element is collapsible in the horizontal and vertical directions. An exemplary compression device can include a bladder 1010 as described previously herein. A surgical drain device is configured (step 1706). The surgical drain device and the wound closure device are placed into the wound (step 1708). The surgical drain device is placed ahead of the wound closure device and the surgical drain device and wound closure device are in contact after placement. Negative pressure is applied at the inlet to cause the compression device to exert pressure on the wound and a surface of the tissue surrounding the wound (step 1710). The pressure exerted by the compression device collapses the drainage element of the wound closure device in the vertical and horizontal directions to approximate wound margins in the undermined portion and wound margins at the surface portion, respectively. The wound is drained of fluids during movement of the wound margins (step 1712). The wound closure device is removed from the wound, and the wound is closed with or without sutures (step 1714). A portion of the surgical drain device remains in the closed wound.

In some embodiments, the wound closure device can define one or more curved axes along which collapsing motion can occur. In an exemplary embodiment, the curved axes can be parallel azimuthal lines at nearly constant radius in a cylindrical coordinate system at different points along the height of the cylinder. The wound closure device can collapse primarily along the curved axis in some embodiments. In some embodiments, the wound closure device can define at least two curved axes that are perpendicular. For example, a first curved axis can be an azimuthal line at nearly constant radius in a cylindrical coordinate system with the height axis across the wound margins and a second curved axis can be an azimuthal line at nearly constant radius in a cylindrical coordinate system with the height axis along the wound margins.

Figure 22:
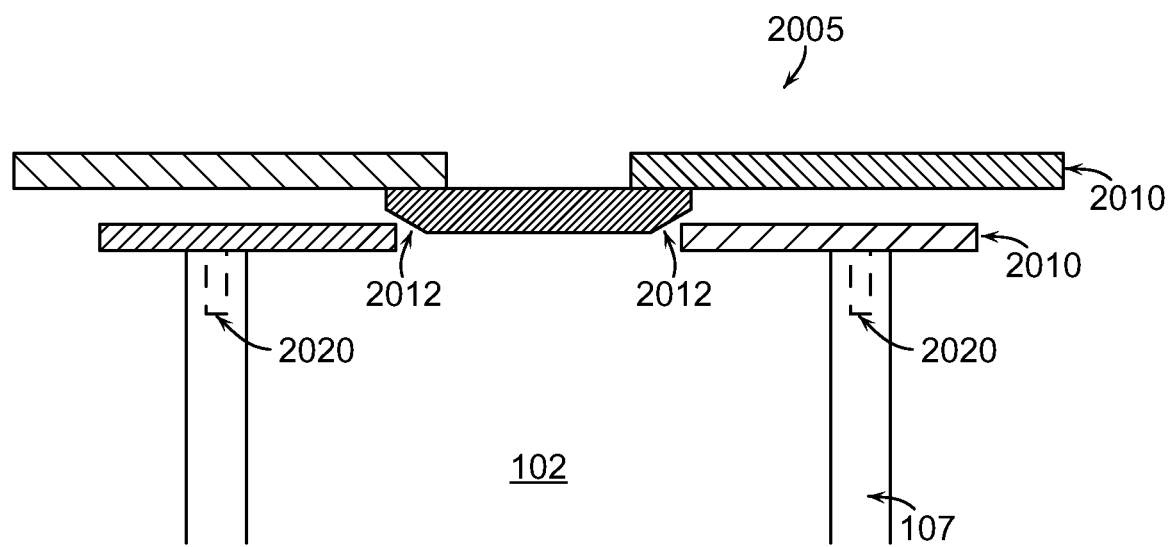
FIG. 22 illustrates a cross-sectional view of the structures shown in FIG. 21.

As shown in FIGS. 21 and 22, the moveable structure 2005 can attach to the collapsible structure 102. The moveable structure 2005 can provide several advantages. In some embodiments, the moveable structure 2005 can provide additional support to the collapsing structure 102 that are substantially perpendicular to the walls 107 to prevent tilting of the compression structure 102 during application of negative pressure. In some embodiments, the structure 2005 operates as an anti-adhesion layer that can prevent tissue within the wound from inhibiting movement of the structure 102. By this contact, the structure 102 can slide freely along the underlying tissue.

In various embodiments, elements of structure 2005 can include, but is not limited to, biocompatible plastics such as polytetrafluoroethylene-based polymers. The structure can be biocompatible and/or sterile in various embodiments.

In exemplary embodiments, the structure 2005 can include scales or lamellae 2010. The scales can be thin with thickness of less than 2 mm and have rounded edges to reduce friction. The shapes and thicknesses can vary across the array of scale elements. The scales 2010 can be layered in the structure 2005 to reduce or prevent gaps that allow tissue ingrowth or adhesion. In some embodiments, each scale 2010 can be attached to the structure 102. For example, each scale can be attached at a pivot point 2002 on a wall 107 where the wall 107 connects to a rigid or semi-rigid membrane 109. In various embodiments, the attachment 2020 between a scale 2010 and the wall 107 can be a mechanical attachment such as a peg or can be an adhesive. The pivot points 2002 can be hinges or flexure points. In some embodiments, the scales 2010 can include channels 2012 along portions of the scale 2010. The channels 2012 can allow fluid flow and scale movement while preventing tissue ingrowth between scales 2010. The scales can overlap adjacent scales, can be dovetailed or interleaved to accommodate relative movement between adjacent scale elements or rows of elements as illustrated. Note, for example, as elements 109 pivot about hinge points 2002, elements on a first side of panel 107 rotate in a first direction 2007 towards panel 107 under negative pressure. Elements 2011 on the opposite side of panel 107 rotate in a second direction 2009 towards the panel 107. In preferred embodiments, the elements 2010, 2011 can be mounted rigidly to the overlying structure 102 at a single point or at a plurality of points for each element. Alternatively, that can rotate around a single point or be limited to rotate through an angle or range. The scale elements can form an array that is used to contract a flat tissue surface or a curved surface or surfaces as described herein. The scales can extend peripherally over skin tissue, for example, or can extend peripherally from a structure positioned within the wound and between tissues and extend laterally from the wound opening. The scales can also be mounted to a domed structure as shown in FIGS. 5A-5D.

Figure 23:
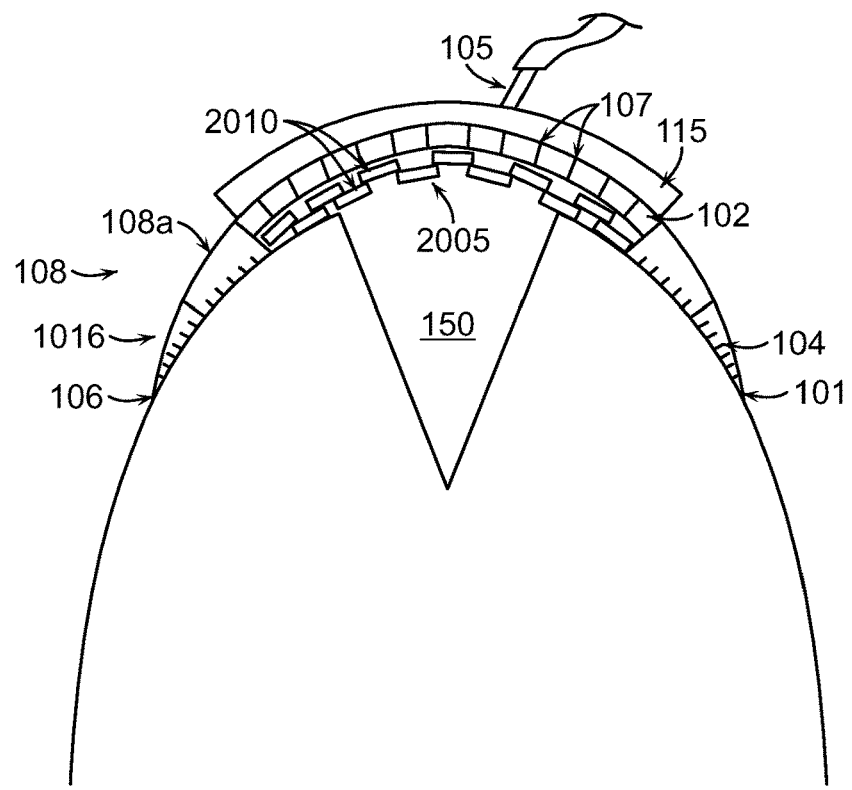
FIG. 23 illustrates a wound closure device including a moving tissue contact structure applied to a wound in accordance with various embodiments of the present application.
Figure 24:
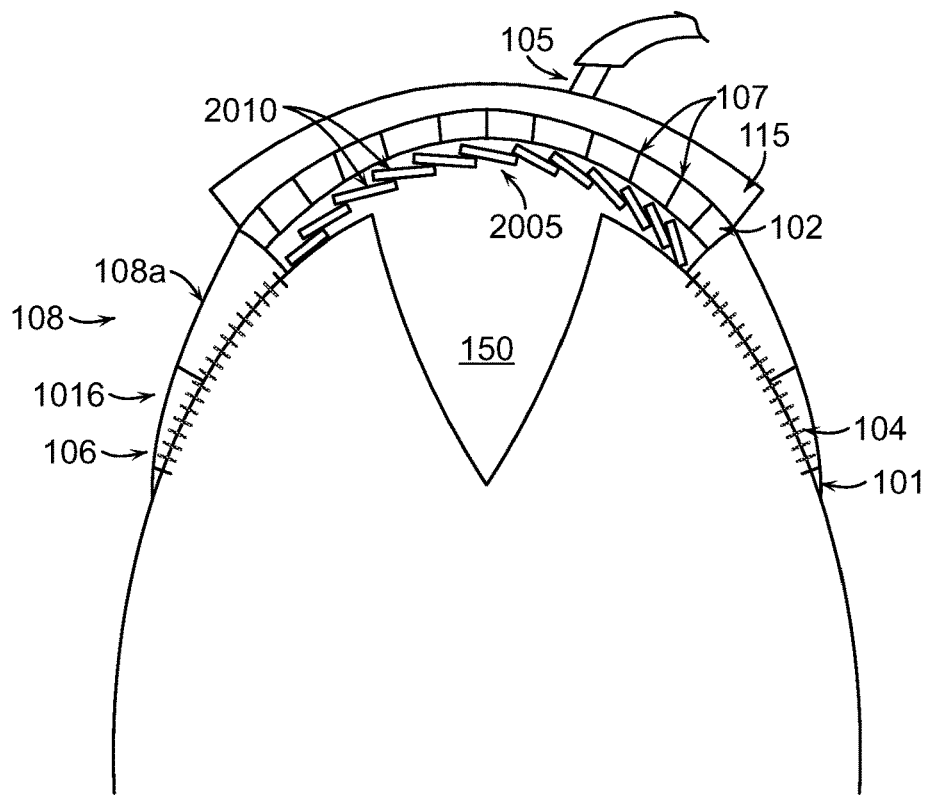
FIG. 24 illustrates a wound closure device including a moving tissue contact structure applied to a wound in accordance with various embodiments of the present application.

FIGS. 23 and 24 illustrate a wound treatment device including structure 2005 in accordance with various embodiments of the present invention. In some embodiments, the structure 2005 can include scales 2010. In some embodiments as shown in FIG. 23, the scales may be interdigitated wherein each of the scales 2010 is located above or below both of its neighbors. In alternative embodiments as shown in FIG. 24, each scale 2010 can be located alternately above and below neighboring scales.

A procedure known as a fasciotomy can be performed to relieve pressure or tension in an area of tissue or muscle and can be used to treat acute compartment syndrome among other conditions. The fasciotomy includes creation of an incision that can be 5 to 10 inches (12.7 to 25.4 cm) long and cutting of the fascia surrounding the muscle to relieve pressure. As a result, muscle often can intrude or bulge out of the wound and make subsequent closure of the wound by bringing together the wound margins significantly more difficult. If the wound is not closed within 7-10 days, for example, the configuration of skin and muscle tissue can "freeze" in place as tissue adhesions take hold. Thus, it can be crucial to address wound closure in as timely a manner as possible. Systems and methods described herein can facilitate closure of fasciotomy wounds and other types of wounds as described previously herein.

Figure 25:
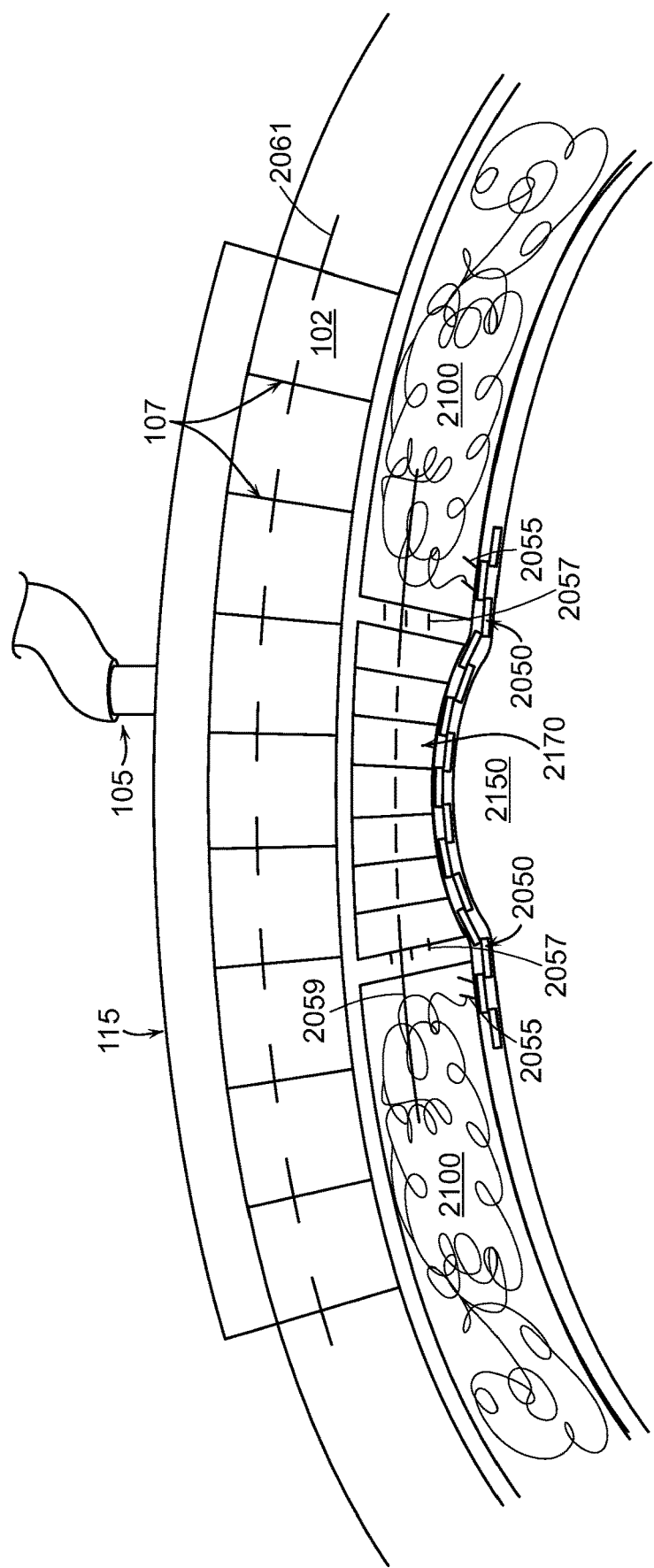
FIG. 25 illustrates a cross-sectional view of a wound closure device including a moving scale structure applied to a fasciotomy wound in accordance with various embodiments of the present invention.
Figure 26:
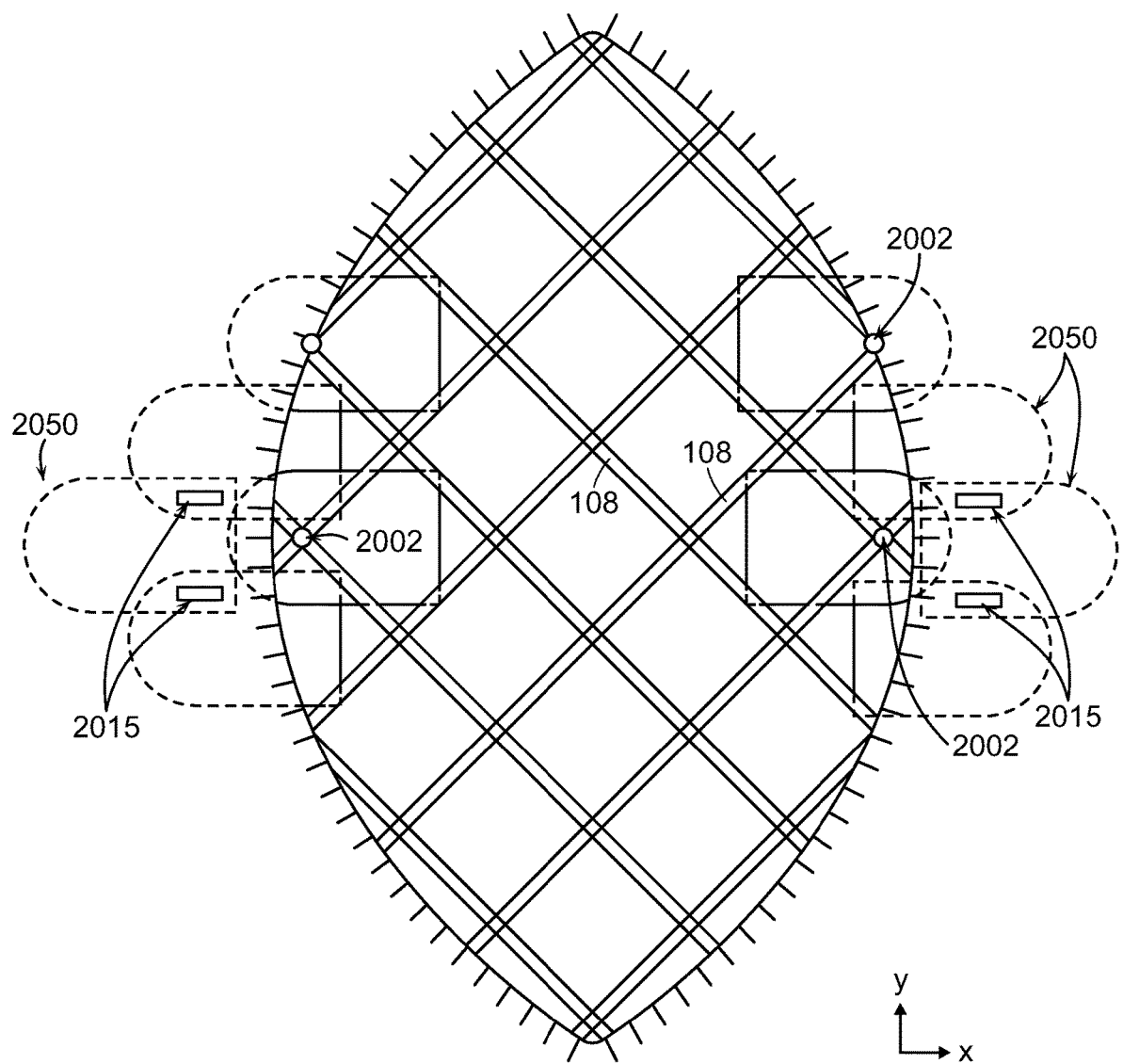
FIG. 26 illustrates a top view of the wound closure device applied to the fasciotomy wound shown in FIG. 25.

FIGS. 25 and 26 illustrate, respectively, a cross-sectional view and a top view of a fasciotomy wound treated by a wound closure device as described herein. As described above, the muscle 2150 can bulge out of the open wound after the fascia is cut. As a result, the fatty tissue 2100 and skin on opposite margins of the incision can resist being brought into close opposition. In a preferred embodiment, the wound closure device can include a first collapsible structure 102 above the wound and a structure 2170 within the wound. In some embodiments, the structure 102 can be similar to that described above with reference to FIG. 6. In other embodiments, the structure 2170 can be similar to the depicted material in FIGS. 25 and 26. For example, the structure 2170 can include a series of first struts or members connected perpendicularly to a series of second struts or members. In various embodiments, the connections between the first struts and second struts can flex or hinge to accommodate collapse of the wound filler material, as provided in FIGS. 7-8 described herein. The first structure 102 can be coupled to, or operate separately from structure 2170. Structure 102 can collapse along a first arcuate path 2061 whereas structure 2170 can collapse along arcuate path 2059. The arcuate paths 2059, 2061 can have the same or different radii of curvature. The structures can collapse at the same rate or at different rates depending upon the morphology of the wound and the treatment protocol.

In another preferred embodiment, the wound closure device 2170 can have tissue anchors 2057 on peripheral surfaces to engage adjacent tissue. Anchors 2057 are described, for example, in U.S. Pat. No. 9,421,132 and also in U.S. Pat. No. 9,597,484, the entire contents of these patents being incorporated herein by reference. Also, scales that extend outside the peripheral edges of structure 2170 can also optionally include tissue anchors 2055 on one or both sides. In the depicted embodiment, anchors 2055 can grasp the overlying tissue 2100, thereby applying a lateral force toward the opposing wound margin to aid in closure while the scales 2050 slide over the underlying tissue 2150.

The structure or wound filler material 2170 can connect to scaled elements 2050 in some embodiments. Alternatively, a layer of scales can be provided separately in which the scales comprising an interconnected array of elements that form a flexible layer positioned between the collapsing structure and a tissue layer such as muscle or facia, or at layer of fat, for a surface of skin or dermis. The elements 2050 can be placed between the underlying muscle tissue 2150 and the skin and/or fatty tissue 2100 to promote relative translation between the components as the wound closes. As the wound closes, the scales 2050 can slide across one another and move or slide relative to the underlying and overlying tissue. The scale elements 2050 can prevent adhesion between the muscle tissue 2150 and the overlying fatty tissue or skin 2100. In some embodiments, the scale elements 2050 and wound filler material 2170 can replace the use of foam in wound recovery.

Figure 27:
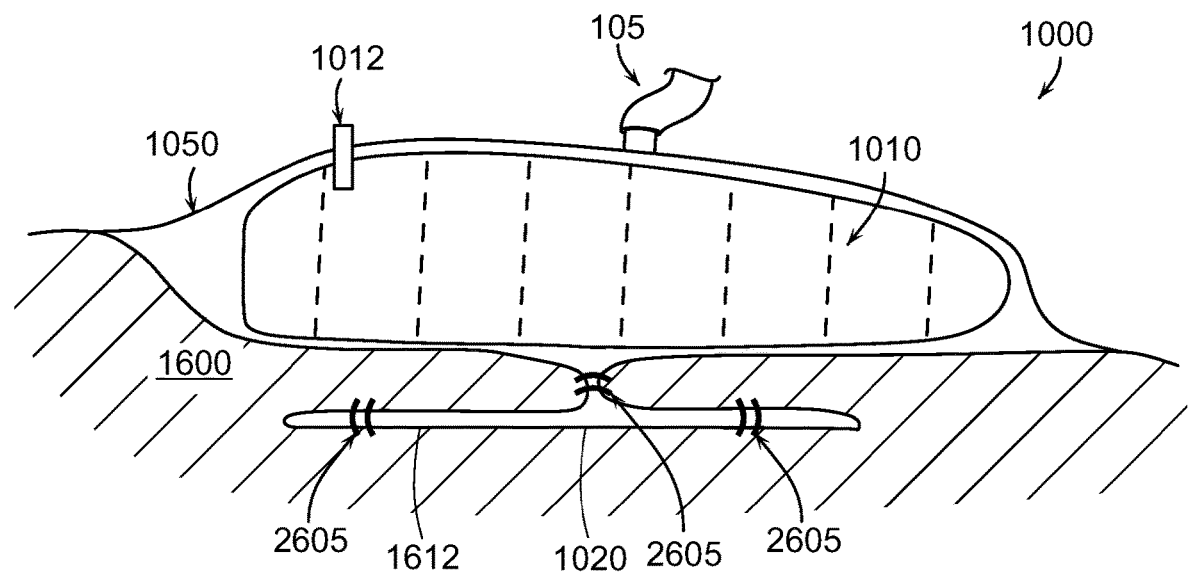
FIG. 27 illustrates a wound closure device applied to a drainless abdominal injury according to various embodiments of the present invention.

FIG. 27 illustrates a wound closure device 1000 that can be applied to an inset wound 1610 at the surface to properly approximate the wound margins in an undermined portion 1612 of the wound. The wound closure device 1000 can be used in treating wounds after "drainless" abdominoplasty, for example. In drainless abdominoplasty, no drain is placed at the completion of an operation to carry accumulating fluids to the surface of the tissue and out of the patient. Some drainless abdominoplasty operations involve the use of progressive tension sutures techniques while others preserve Scarpa fascia or sub-Scarpa fascia fat. At the end of an operation, sutures 2605 may be placed to help secure tissue in the undermined area 1020 and at the tissue surface. Alternatively, the systems and methods described herein for reduced suturing or sutureless wound closure can also be employed. The bladder 1010 of the wound closure device 2600 can generate downward pressure on the wound to aid the tissue above and below the undermined portion at approximating and promote tissue granulation and healing while minimizing the risk of seroma.

The wound closure device 1000 can be applied in several stages. First, the deflated bladder 1010 can be placed over the wound and the drape 1050 can be pulled taut over the bladder 1010 and secured to surrounding tissue at the perimeter of the drape 1050. Next, the bladder can be inflated through the inlet 1012. As the bladder 1010 inflates, it is confined between the tissue surface and the drape 1050 and the pressure inside the bladder 1010 begins to increase. As a result, the pressure on the tissue causes the overhanging tissue in the undermined portion to press down on the base of the wound and stabilize.

In some embodiments, the wound and overlying tissue layers can be substantially concave. This type of wound can be difficult to heal because force cannot be leveraged from adjacent or surrounding tissue into the depression caused by the concavity. Systems and methods described herein can address this difficulty by providing the inflated bladder 1010 confined by the drape 1050. In some embodiments, the volume of the inflated bladder 1010 is such that it can still apply a sufficient pressure to the concave wound to stabilize the tissue layers within the wound.

Figure 28A:
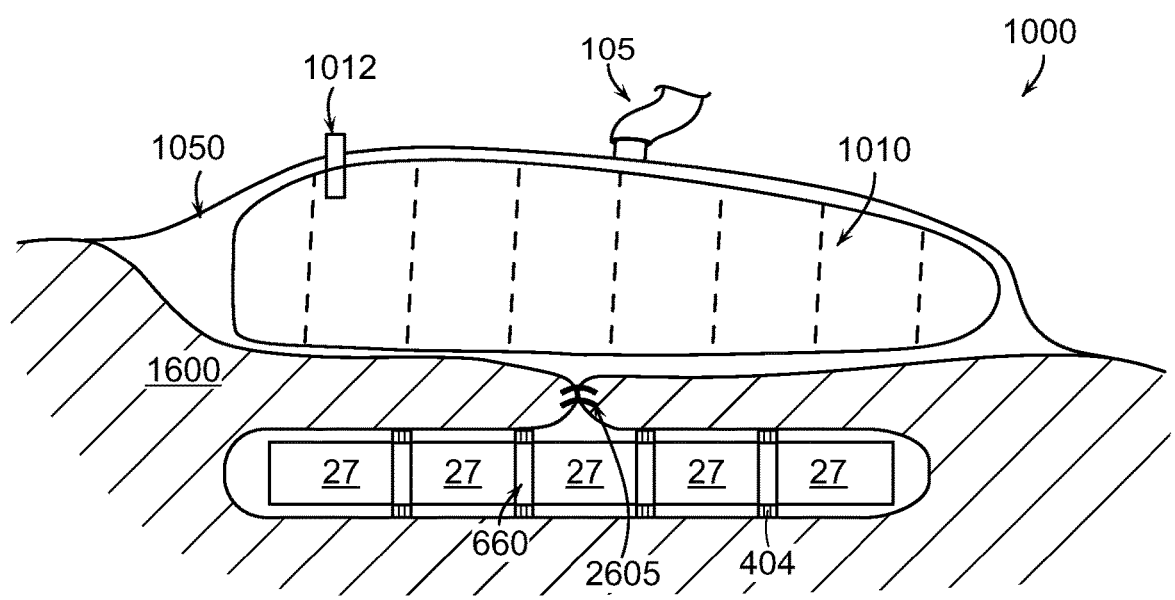
FIG. 28A illustrates a wound closure device that includes a surgical drain device in accordance with various embodiments of the present invention.

FIG. 28A illustrates the wound closure device 1000 placed over a wound that has been sutured closed in keeping with the principles of drainless surgical techniques. The wound includes a surgical drain device 660 as described previously with regard to FIGS. 11, 12A-12E, and 15E. In this embodiment, the surgical drain device 660 can be placed without drains 30 as in earlier embodiments. The apertures 27 extend through the device such that tissue on opposing sides extends into and through the device. In this embodiment, the surgical drain device 660 can help prevent the formation of voids that can lead to seroma while pulling opposing portions of tissue into alignment using tissue anchors 28, 404 as described above. In some embodiments, the surgical drain device 660 includes entirely biodegradable materials such that the device is absorbed into the body tissue as the tissue heals and closes the wound.

Figure 28B:
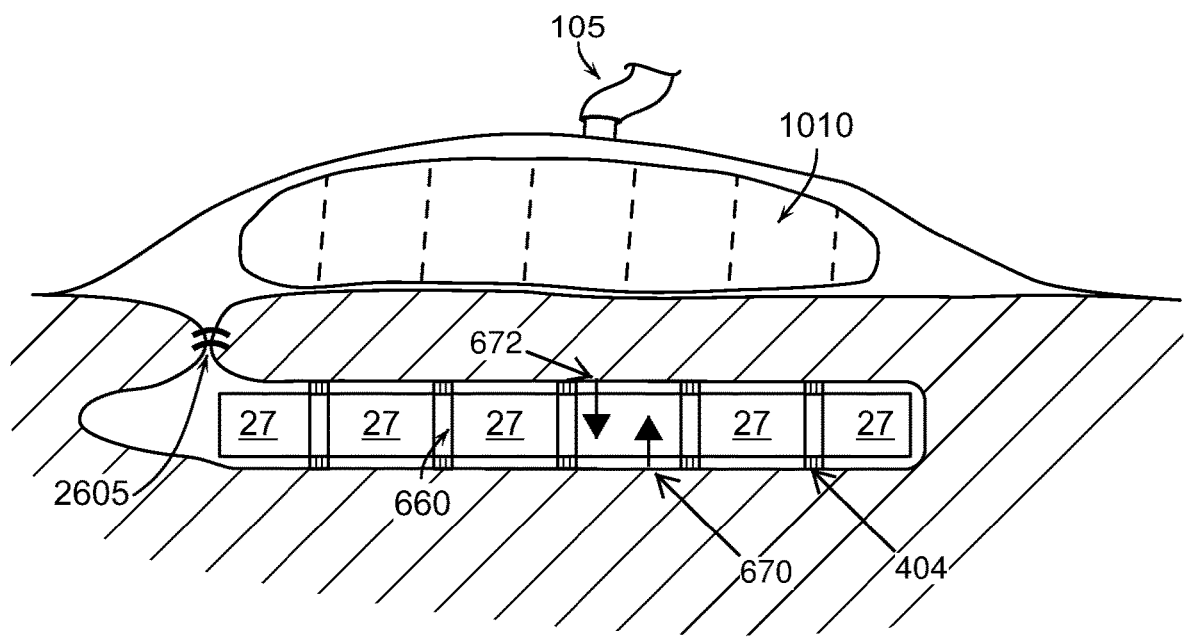
FIG. 28B illustrates a wound closure device that includes a surgical drain device applied to an offset wound in accordance with various embodiments of the present invention.

FIG. 28B illustrates a wound closure device placed into an offset wound that can be created as a result of some surgical procedures. The device can be placed not over the suture or opening to the wound or injury but offset to the side as shown. The device can provide downward pressure onto the overlying flap to cause the flap to maintain contact with the more internal portion of tissue and to reduce micromotion between tissue surfaces. Although the embodiment shown in FIG. 28B is a "drainless" closure, the surgical drain device 660 can include drains in some embodiments and a drain can be placed that exits the wound to bring fluids and effluvia to the surface and out of the patient.

FIG. 28B depicts the device 660 before the application of negative pressure that causes the tissue anchors 404 (optional) to be directed into the tissue on opposite sides and also causes displacement 670, 672 of tissue portions into apertures 27 from both sides to contact one another and fill the apertures.

Figure 29:
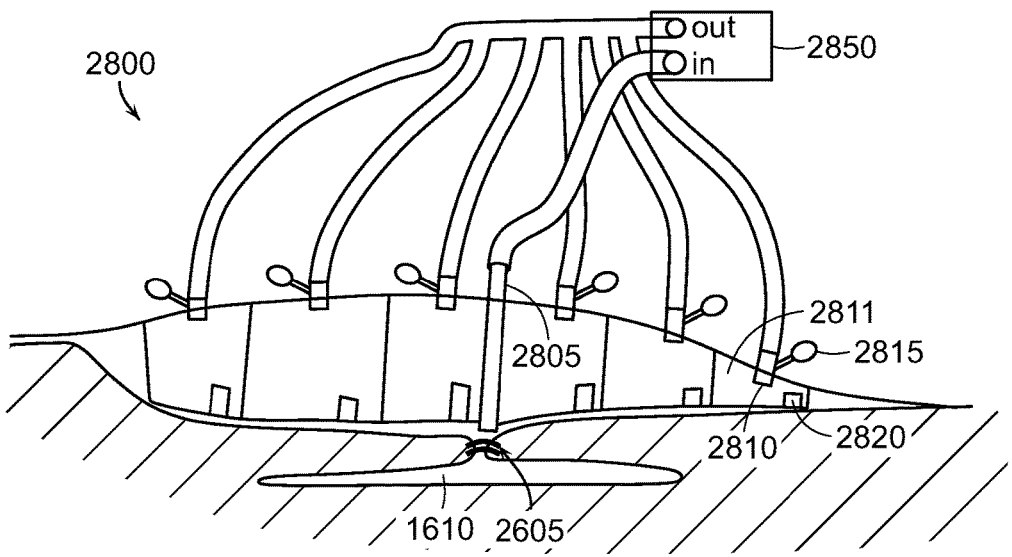
FIG. 29 illustrates a wound closure device having inflatable sections applied to a drainless abdominal injury according to various embodiments of the present invention.

FIG. 29 illustrates a wound closure device 2800 in accordance with various embodiments described herein. The wound closure device 2800 includes individual inflatable sections 2811 that can be individually inflated. In some embodiments, the inflatable sections are similar to those described above with respect to FIG. 16E. For example, the inflatable sections 2811 can be modular in some embodiments. The use of individual inflatable sections 2811 allows for application of different levels of pressure at different locations along the wound. For example, some tissue areas in the wound may naturally lie closely opposite with little lateral movement while others may naturally include larger gaps where opposing tissues do not approximate well. Such poorly approximated areas may require a higher level of pressure or a greater volume of air in the individual section overlying the area to reach the requisite pressure.

In some embodiments, each inflatable section 2811 can have an inlet 2810 to allow inflation of the section. In some embodiments, a pressure regulator 2815 can be located near the inlet 2810 to supply a consistent air pressure. In some embodiments, the pressure regulator 2815 can act as a vent that prevents overpressure inside the inflatable section. In some embodiments, the pressure regulator 2815 can be operatively connected to a sensor 2820 within the inflatable member 2811. If the sensor detects an overpressure condition, the pressure regulator 2815 can vent the inflatable member until an appropriate pressure is reached.

In various embodiments, the sensor 2820 can include a pressure sensor that directly detects the pressure within each of the inflatable members. In some embodiments, the sensor 2820 can measure the gas or fluid pressure directly in each section or indirectly through its effect on the tissue. For example, the sensor 2820 can include an optical sensor that can perform a colorimetric measurement on the tissue and determine a level of perfusion of the tissue. If perfusion is minimal, it may be an indication that the wound closure device 1000 is pressing too hard on the tissue and cutting off blood flow in the microvasculature. In such an embodiment, the pressure regulator 2815 can receive a signal to reduce the pressure at that area until normal perfusion is restored.

A pump 2850 can provide positive pressure, negative pressure, or both to the wound closure device 1000. The pump 2850 can be connected to a drain outlet 2805 to provide negative pressure to the interior of the wound closure device. Negative pressure applied through the drain outlet 2805 can help the inflatable sections 2811 apply pressure to the wound. In addition, any fluid that exits through the stitches 2605 can be pulled out of the wound closure device 1000 and into the pump 2850.

The pump 2850 can also provide the positive pressure needed to inflate the inflatable sections 2811. In some embodiments, a manifold can be used to connect a single pump 2850 to a myriad of inflatable sections 2811 simultaneously. In alternative embodiments, separate tubes can be used to connect the inlet 2810 of each inflatable section 2811 with separate pumps 2850. The manifold can include valves that close off individual lines to individual inflatable sections 2811.

The pump 2850 can be mechanical, electrical, or hand-operated (e.g., a syringe pump). Although a single pump 2850 is shown in FIG. 29, multiple pumps including a mixture of mechanical, electrical, and hand-operated pumps can be used with systems and methods described herein. An exemplary pump for use with systems and embodiments described herein can include the SNAP™ Therapy Cartridge (Acelity, San Antonio, Tex.).

Figure 30:
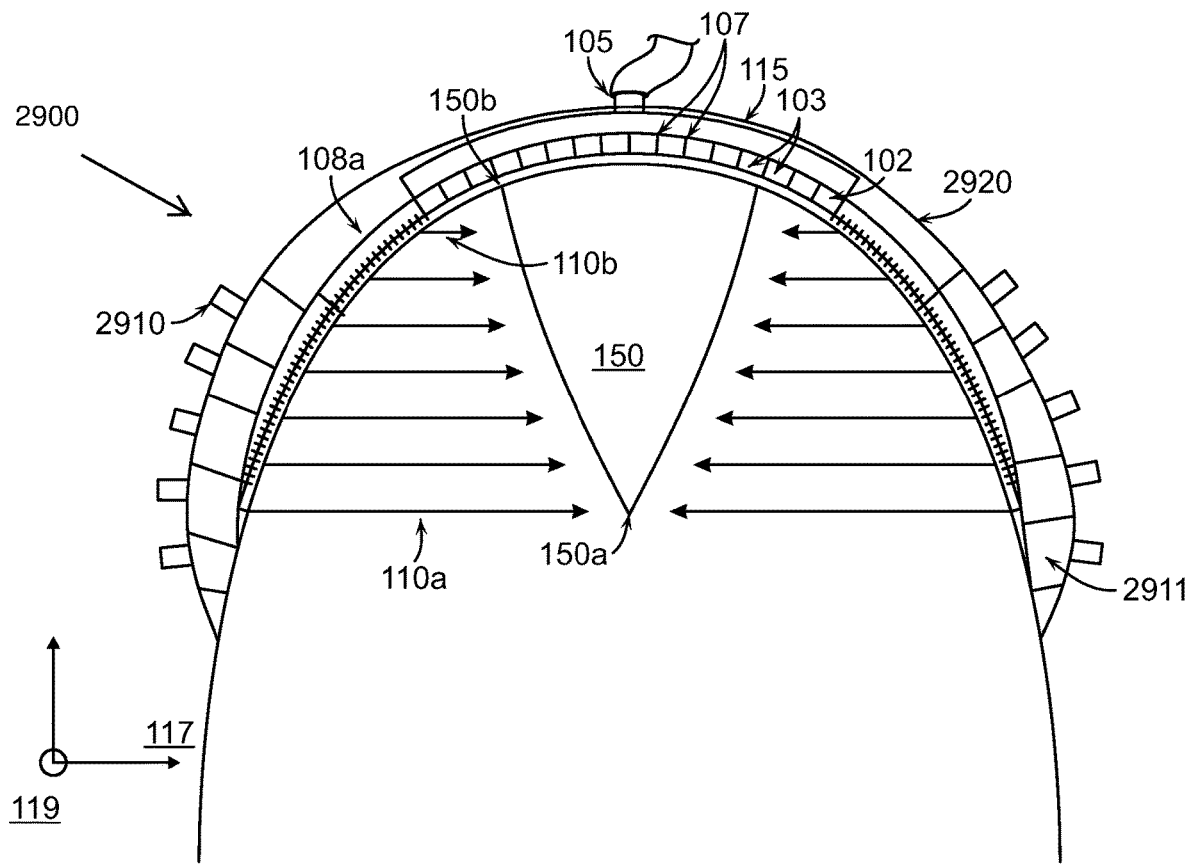
FIG. 30 illustrates a wound closure device applied to a wound in accordance with various embodiments of the present invention.

In some embodiments, inflatable bladder sections 2811 can be used in conjunction with systems and methods described herein to promote healing of wounds 150 at extremities caused, for example, as a result of amputation. As shown in FIG. 30, the wound closure device 2900 can be applied substantially as described above with reference to FIGS. 1-4. A drape 2920 can be placed over the wound closure device and inflatable sections 2911 of a bladder in a deflated state. The edge of the drape 2950 can be secured to adjacent, unaffected tissue away from the wound. Then, each inflatable section 2911 can be inflated using an inlet 2910 to apply inward pressure to cause the wound 150 to close from the deepest portion 150a to the shallowest portion 150b.

In some embodiments, a sequential inflation procedure can be used to apply pressure in stages as the wound 150 closes from deep to shallow. The inflatable sections 2911 nearest the edge of the drape 2920 can first be inflated to create pressure laterally at the deepest portion. Next, the adjacent inflatable sections 2911 can progressively be inflated in sequence until even the inflatable sections 2911 laterally adjacent to the shallowest portion 150b of the wound 150 are inflated. This sequence can progress over time periods from seconds to minutes to days as tissue healing proceeds.

While the present inventive concepts have been described with reference to particular embodiments, those of ordinary skill in the art will appreciate that various substitutions and/or other alterations may be made to the embodiments without departing from the spirit of the present inventive concepts. Accordingly, the foregoing description is meant to be exemplary and does not limit the scope of the present inventive concepts.

A number of examples have been described herein. Nevertheless, it should be understood that various modifications may be made. For example, suitable results may be achieved if the described techniques are performed in a different order and/or if components in a described system, device, or method are combined in a different manner and/or replaced or supplemented by other components or their equivalents. Accordingly, other implementations are within the scope of the present inventive concepts.

The invention claimed is:

1. A negative pressure wound closure device to treat a wound comprising;
    a collapsible structure positionable external to a wound opening, wherein the collapsible structure extends over at least a portion of tissue of the wound opening, the collapsible structure having articulating elements that are displaced during movement of spaced apart wound margins of the wound opening; and a plurality of scale elements positioned between the structure and a tissue surface, the plurality of scale elements mechanically attached to the collapsible structure and configured to slide over the tissue surface during movement of the wound margins.

2. The device of claim 1 further comprising a flap having a first portion and a second portion wherein the first portion is relatively more elastic than the second portion.

3. The device of claim 2 wherein the flaps are attached to a wrap using a first plurality of anchoring elements.

4. The device of claim 1 wherein the collapsible structure further comprises a compression element that contacts the portion of tissue adjacent the wound opening including a stiff edge, wherein scale elements are mechanically attached to pivot joints of the collapsible structure, wherein the scale elements have an anti-adhesion surface that contacts the tissue surface such that the scale elements slide on the tissue surface during movement of wound margins.

5. The device of claim 1 further comprising a drape that affixes a lateral portion of the structure to tissue surrounding at least a deep portion of the wound.

6. The device of claim 5 wherein the structure is configured such that negative pressure applied causes the structure to at least partially collapse and causes the lateral portion to apply an inward force to the deep portion of an amputation wound to close before the shallow portion.

7. The device of claim 1 wherein a radius of curvature of the structure is different from a radius of curvature of the tissue surrounding the wound.

8. The device of claim 1 wherein the collapsible structure includes a plurality of cells.

9. The device of claim 8, wherein at least two cells in the plurality of cells have different internal cell sizes.

10. The device of claim 8, wherein a density of the plurality of the cells varies across the collapsible structure.

11. The device of claim 8 wherein the cells have different sizes and shapes that are configured to have a force distribution that is varied across the device.

12. The device of claim 1 wherein the wound closure device comprises a plurality of pivot points that are mechanically attached to a corresponding plurality of scale elements.

13. The device of claim 1, wherein the collapsible structure includes a micropore material.

14. The device of claim 13, wherein a pore size of micropores in the micropore material in a first portion of the collapsible structure is different than a pore size of micropores in the micropore material in a second portion of the micropore material.

15. The device of claim 13, wherein a density of micropores in the micropore material in a first portion of the collapsible structure is different than a density of micropores in the micropore material in a second portion of the micropore material.

16. The device of claim 1 wherein the wound closure device comprises one or more walls or stabilizer elements.

17. The device of claim 1 wherein the wound closure device comprises a curved peripheral surface that contacts the wound margins.

18. The device of claim 1 wherein at least a portion of the collapsible structure extends over the wound margins.

19. The device of claim 1 wherein the collapsible structure is configured to be disposed between the wound margins.

20. The device of claim 1 wherein different portions of the collapsible structure are configured to collapse at different rates upon application of negative pressure.

21. The device of claim 1 wherein the scale elements extend laterally from the collapsible structure to a position under overlying tissue or to a position over tissue including the wound margins or a combination thereof.

22. The device of claim 1 wherein the scale elements are mechanically attached to the collapsible structure with pegs.

23. The device of claim 1 wherein the scale elements are mechanically attached to the collapsible structure with an adhesive.

24. The device of claim 1 wherein the scale elements have a thickness of less than 2 mm.

25. A negative pressure wound closure device to treat a wound comprising;
a collapsible structure positionable external to a wound opening, the collapsible structure that extends between wound margins of the wound opening over at least a portion of tissue within the wound opening, the collapsible structure having a periphery in contact with the wound margins and further includes articulating elements that are displaced during movement of spaced apart wound margins during closure of the wound opening upon the application of negative pressure; and
a plurality of connected scale elements positioned between the structure and a tissue surface wherein a portion of the scale elements extend beyond the periphery of the collapsible structure such that the portion of the scale elements are positioned between overlying and underlying tissue and configured to slide upon tissue surfaces during movement of the wound margins.

26. The device of claim 25 wherein the scale elements are connected to pivot joints of the collapsible structure, and wherein the scale elements have an anti-adhesion surface that contacts the tissue surface such that the scale elements slide on a tissue surface during movement of wound margins.

27. The device of claim 25 wherein a radius of curvature of the structure is different from a radius of curvature of tissue surrounding the wound.

28. The device of claim 25 wherein the collapsible structure includes a plurality of cells.

* * * * *